(12) United States Patent
Bi et al.

(10) Patent No.: US 11,572,283 B2
(45) Date of Patent: Feb. 7, 2023

(54) MOLECULAR SIEVE HAVING MESOPORES, PREPARATION METHOD THEREFOR, AND APPLICATION THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Yunfei Bi, Beijing (CN); Guofu Xia, Beijing (CN); Mingfeng Li, Beijing (CN); Qinghe Yang, Beijing (CN); Weiguo Huang, Beijing (CN); Qingzhou Guo, Beijing (CN); Wenxiu Fang, Beijing (CN); Luqiang Wang, Beijing (CN); Hongbao Li, Beijing (CN); Honghui Li, Beijing (CN); Jie Gao, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 58 days.

(21) Appl. No.: 16/759,225

(22) PCT Filed: Oct. 26, 2018

(86) PCT No.: PCT/CN2018/112072
§ 371 (c)(1),
(2) Date: Apr. 24, 2020

(87) PCT Pub. No.: WO2019/080922
PCT Pub. Date: May 2, 2019

(65) Prior Publication Data
US 2020/0325029 A1  Oct. 15, 2020

(30) Foreign Application Priority Data

Oct. 26, 2017 (CN) ......................... 201711016098.X
Oct. 26, 2017 (CN) ......................... 201711016179.X

(51) Int. Cl.
*B01J 29/04* (2006.01)
*C01B 39/04* (2006.01)
(Continued)

(52) U.S. Cl.
CPC ............... *C01B 39/04* (2013.01); *B01J 6/001* (2013.01); *B01J 29/041* (2013.01); *B01J 29/042* (2013.01);
(Continued)

(58) Field of Classification Search
CPC ....... C01B 39/04; C01B 39/065; C01B 39/46; C01B 39/54; C01B 39/10; C01B 39/12; B01J 6/001; B01J 37/0203; B01J 37/031; B01J 37/10; B01J 37/036; B01J 35/1019; B01J 35/1061; B01J 35/002; B01J 35/1014; B01J 35/1057; B01J 35/109; B01J 2229/20; B01J 2229/40; B01J 2229/42; B01J 29/041; B01J 29/042; B01J 29/043; B01J 29/044; B01J 29/405; B01J 29/7057; B01J 29/7084; B01J 29/7092; B01J 29/7096; B01J 29/7261; B01J 29/7269; B01J 29/7284; B01J 29/7292; B01J 29/7461; B01J 29/7484; B01J 29/7215; B01J 29/7615; B01J 29/7684; B01J 29/7007; B01J 29/7042; B01J 29/85;
(Continued)

(56) References Cited

U.S. PATENT DOCUMENTS 4,419,420 A   12/1983 Ishizaki
4,518,485 A   5/1985 Lapierre et al.
(Continued)

FOREIGN PATENT DOCUMENTS

CN   1350981 A   5/2002
CN   1565969 A   1/2005
(Continued)

OTHER PUBLICATIONS

Verboekind et al., "Mesoporous ZSM-22 zeolite obtained by desilication: peculiaritites associated with crystal morphology and aluminum distribution", CrystEngComm, 2011, 13, pp. 3408-3416.*

(Continued)

*Primary Examiner* — Elizabeth D Wood
(74) *Attorney, Agent, or Firm* — Novick, Kim & Lee, PLLC; Allen Xue

(57) ABSTRACT

A molecular sieve has a silica/alumina molar ratio of 100-300, and has a mesopore structure. One closed hysteresis loop appears in the range of $P/P_0=0.4$-$0.99$ in the low temperature nitrogen gas adsorption-desorption curve, and the starting location of the closed hysteresis loop is in the range of $P/P_0=0.4$-$0.7$. The catalyst formed from the molecular sieve as a solid acid not only has a good capacity of isomerization to reduce the freezing point, but also can produce a high yield of the product with a lower pour point. The process for preparing the catalyst involves steps including crystallization, filtration, calcination, and hydrothermal treatment.

17 Claims, 12 Drawing Sheets

(51) Int. Cl.

| | |
|---|---|
| B01J 29/40 | (2006.01) |
| B01J 29/70 | (2006.01) |
| B01J 29/72 | (2006.01) |
| B01J 29/74 | (2006.01) |
| C01B 39/46 | (2006.01) |
| C01B 39/12 | (2006.01) |
| B01J 6/00 | (2006.01) |
| C01B 39/10 | (2006.01) |
| C01B 39/54 | (2006.01) |
| C01B 39/06 | (2006.01) |
| B01J 37/03 | (2006.01) |
| B01J 37/02 | (2006.01) |
| B01J 37/10 | (2006.01) |
| B01J 35/10 | (2006.01) |
| B01J 37/00 | (2006.01) |
| B01J 35/00 | (2006.01) |
| B01J 29/76 | (2006.01) |
| B01J 29/85 | (2006.01) |
| B01J 29/86 | (2006.01) |
| B01J 29/87 | (2006.01) |
| B01J 29/88 | (2006.01) |
| C07C 5/22 | (2006.01) |
| C10G 45/64 | (2006.01) |
| C10G 45/60 | (2006.01) |
| C10G 45/62 | (2006.01) |

(52) U.S. Cl.
CPC ........... *B01J 29/043* (2013.01); *B01J 29/044* (2013.01); *B01J 29/405* (2013.01); *B01J 29/7007* (2013.01); *B01J 29/7042* (2013.01); *B01J 29/7057* (2013.01); *B01J 29/7084* (2013.01); *B01J 29/7092* (2013.01); *B01J 29/7096* (2013.01); *B01J 29/7215* (2013.01); *B01J 29/7261* (2013.01); *B01J 29/7269* (2013.01); *B01J 29/7284* (2013.01); *B01J 29/7292* (2013.01); *B01J 29/7461* (2013.01); *B01J 29/7615* (2013.01); *B01J 29/7684* (2013.01); *B01J 29/85* (2013.01); *B01J 29/86* (2013.01); *B01J 29/87* (2013.01); *B01J 29/88* (2013.01); *B01J 35/002* (2013.01); *B01J 35/109* (2013.01); *B01J 35/1014* (2013.01); *B01J 35/1019* (2013.01); *B01J 35/1057* (2013.01); *B01J 35/1061* (2013.01); *B01J 35/1066* (2013.01); *B01J 37/0018* (2013.01); *B01J 37/0203* (2013.01); *B01J 37/031* (2013.01); *B01J 37/036* (2013.01); *B01J 37/10* (2013.01); *C01B 39/065* (2013.01); *C01B 39/10* (2013.01); *C01B 39/12* (2013.01); *C01B 39/46* (2013.01); *C01B 39/54* (2013.01); *C07C 5/22* (2013.01); *C07C 5/222* (2013.01); *C07C 5/2206* (2013.01); *C07C 5/2213* (2013.01); *C10G 45/60* (2013.01); *C10G 45/62* (2013.01); *C10G 45/64* (2013.01); *B01J 2229/20* (2013.01); *B01J 2229/40* (2013.01); *B01J 2229/42* (2013.01)

(58) Field of Classification Search
CPC ... B01J 29/86; B01J 29/87; B01J 29/88; B01J 35/1066; B01J 37/0018; C10G 45/64; C10G 45/62; C10G 45/60; C07C 5/22; C07C 5/2206; C07C 5/2213; C07C 5/222
USPC ...... 502/60, 61, 63, 64, 66, 74, 77; 423/700, 423/702, 704, 707, 713, 716; 585/671, 585/734, 739, 740
See application file for complete search history.

(56) References Cited

U.S. PATENT DOCUMENTS

| | | |
|---|---|---|
| 5,075,269 A | 12/1991 | Degnan et al. |
| 5,110,445 A | 5/1992 | Chen et al. |
| 5,135,638 A | 8/1992 | Miller |
| 5,200,168 A | 4/1993 | Apelian et al. |
| 5,282,958 A | 2/1994 | Santilli et al. |
| 5,300,210 A | 4/1994 | Zones et al. |
| 5,397,454 A | 3/1995 | Zones et al. |
| 5,990,371 A | 11/1999 | Martens et al. |
| 6,800,266 B2 | 10/2004 | Pinnavaia et al. |
| 7,482,300 B2 | 1/2009 | Lai et al. |
| 2014/0162867 A1* | 6/2014 | Lai .................. B01J 29/40 502/77 |
| 2016/0257623 A1 | 9/2016 | Jan et al. |
| 2018/0134637 A1 | 5/2018 | Lai et al. |

FOREIGN PATENT DOCUMENTS

| | | |
|---|---|---|
| CN | 1683245 A | 10/2005 |
| CN | 1769169 A | 5/2006 |
| CN | 101230290 A | 7/2008 |
| CN | 102050459 A | 5/2011 |
| CN | 102602958 A | 7/2012 |
| CN | 102869753 A | 1/2013 |
| CN | 103073020 A | 5/2013 |
| CN | 103964458 A | 8/2014 |
| CN | 104353484 A | 2/2015 |
| CN | 104812703 A | 7/2015 |
| CN | 104891526 A | 9/2015 |
| CN | 105521818 A | 4/2016 |
| EP | 2085360 B1 | 5/2014 |

OTHER PUBLICATIONS

Groen et al., "Mesoporous beta zeolite obtained by desilication", Mircroporous and Mesoporous Materials, 114, 2008, pp. 93-102.*
Liu et al., "Synthesis, characterization and isomerization performance of micro/mesoporous materials based on H-ZSM-22 zeolite", Journal of Catalysis, 335, 2016, pp. 11-23.*
Parmar et al., "Hydroisomerization of Long Chain n-Paraffins over Pt/ZSM-22: Inluence of Si/Al Ratio", Energy & Fuels, 29, 2015, pp. 1066-1075.*

* cited by examiner

MOLECULAR SIEVE HAVING MESOPORES, PREPARATION METHOD THEREFOR, AND APPLICATION THEREOF

TECHNICAL FIELD

The present invention relates to a molecular sieve having mesopores and its preparation process and application. More specifically, the present invention relates to a high silica-alumina ratio molecular sieve having mesopores, a process for preparing the molecular sieve, a catalyst containing the molecular sieve and its application.

BACKGROUND

Molecular sieve material typically has a high acidity and a high specific surface area, at the same time, the molecular sieve material has a strong chemical stability and a hydrothermal stability, and it is difficult to be damaged by the reactants due to corrosion and dissolution, and therefore is an excellent solid acid catalyst. Different from commonly used homogeneous catalysts, molecular sieve material catalysts can be directly reused without the need of separation, and do not cause the pollution to the environment and contamination in the product. In addition, the parameters of the molecular sieve material such as the specific surface area and the pore-channel structure have a significant impact on the molecular sieve characteristics such as catalytic performance, and thus the preparation of molecular sieves with a special specific surface area or a special pore-channel is an important research direction in the chemical industry field.

For example, in U.S. Patent Applications U.S. Pat. Nos. 4,518,485, 5,990,371, 5,135,638, 4,419,420, 5,110,445 and the like have been reported methods of isomerization and dewaxing technology to produce the base oil of the lubricating oil, in which the molecular sieves used as the acidic component mainly comprise MOR, ZSM-22, ZSM-23, ZSM-48, SAPO-11, SAPO-31, SAPO-41, Nu-10, KZ-2 and the like, and paraffin hydrocarbons can undergo the isomerization reaction to some extent with these molecular sieve materials. However, for these molecular sieves, due to their own properties, usually only a part of the reactants can undergo the isomerization reaction, and the rest of the reactants undergo the cracking reaction, and accordingly the greater the isomerization degree is, the higher the proportion of the cracking reaction is, eventually resulting in a decrease in the yield of the product.

U.S. Patent application U.S. Pat. No. 5,282,958 discloses a catalyst for isomerization and dewaxing. The catalyst contains a mesopore molecular sieve, such as ZSM-5, ZSM-22, ZSM-23, ZSM-11 and the like. U.S. Patent applications U.S. Pat. Nos. 7,482,300 and 5,075,269 disclose an isomerization catalyst containing ZSM-48. U.S. Patent application U.S. Pat. No. 8,513,150 discloses a Y-type molecular sieve having mesopores, in this patent application, the Y-type molecular sieve is firstly calcined at a lower temperature and then calcined in a water-vapor containing gas at a higher temperature (1250° F.–1450° F.), and the mesopore structures are formed in the calcined molecular sieve, and the proportion of the larger mesopore to the smaller mesopore is 5 or more. U.S. Patent application U.S. Pat. No. 5,397,454 discloses a hydrogenation conversion method with a calcined H-type molecular sieve having a small crystal grain size and a constraint index of 13 or more (e.g. SSZ-32), wherein the catalyst has a molar ratio of silica to alumina of greater than 20 and less than 40. U.S. patent application U.S. Pat. No. 5,300,210 also relates to a hydrocarbon conversion method with SSZ-32. U.S. Patent application U.S. Pat. No. 5,300,210 discloses SSZ-32 which is not limited to small crystal grain size. U.S. Patent application U.S. Pat. No. 7,141,529 discloses a method for the metal modification of the molecular sieve with different metals (selected from Ca, Cr, Mg, La, Ba, Pr, Sr, K and Nd metals and Group VIII metal) to provide a catalyst having an improved isomerization selectivity in case that the nC-16 feedstock is used, according to the method used in this patent application, the support is shaped and then impregnated with a liquid containing metal ions so that the modification metals are supported on the molecular sieve.

In addition, the Beta molecular sieve is the only zeolite having a three-dimensional system of twelve-membered ring and straight channels. This unique pore-channel structure and acidity allow the Beta molecular sieve to have a high catalytic activity for hydrocracking and hydroisomerization, an adsorption capacity for linear paraffins, and a good resistance to sulfur and nitrogen poisoning. Generally, in the petrochemical industry, it can be used in the preparation of a catalyst useful in various conversion reactions such as the preparation of cumene by the alkylation reaction of benzene with propylene. In addition, the Beta molecular sieve used in combination with USY can improve the octane number of gasoline. And, in the field of fine chemicals, the Beta molecular sieve also has good activity and selectivity in the aspect of the dehydration and the amine removal.

CN1350981A discloses a process for preparing a high-silica Beta zeolite, which mainly includes the following steps: firstly the crystallized Beta zeolite slurry is exchanged with ammonium, filtered, dried and calcined to remove the template agent, treated with an organic acid or an inorganic acid, and finally hydrothermally treated under pressure to ultimately produce a Beta zeolite having a silica-alumina ratio of 60-80. CN1769169A discloses a process for synthesizing a Beta zeolite having a gradient pore-channel, wherein the resulting Beta zeolite has a silica-alumina ratio of 80-120 and three pore diameter distributions of 0.1-1.7 nm, 1.7-6 nm and 10-90 nm, thus resulting in that the surface utilization rate of the Beta zeolite is greatly increased, however the micropore volume of the resulting zeolite is not large enough, the contribution to the pore volume is mainly from mesopores and macropores (the ratio of the total volume of mesopores and macropores to the total pore volume is 67% or more).

CN104353484A discloses a process for preparing a cheap strong acidic Beta zeolite having multilevel pores, and is going to solve the problem that the molecular sieve of the Beta zeolite having multilevel pores shows a reduced acidity after the desiliconizing treatment. CN103964458A discloses a Beta zeolite having a high silica-alumina ratio and a multilevel pore-channel and a preparation process thereof, the preparation process of said patent application is simply operated and efficient. The resulting Beta zeolite having a high silica-alumina ratio and a multilevel pore-channel has a very strong acid stability, a thermal stability, a hydrothermal stability and a good diffusion performance.

In addition, in the patent documents of CN102602958A, CN103073020A, CN104891526A, CN1683245C, CN102050459A and CN1565969A are disclosed the processes for preparing the zeolite molecular sieve having a certain pore-channel.

However, the current zeolite molecular sieves still have insufficient satisfactory properties such as the lower proportion of mesopore surface area and the lower silica-alumina ratio, and therefore when such a molecular sieve is used as the catalyst or used as the support of the catalyst, there is much room for imporvement of the catalytic property of the catalyst.

SUMMARY OF THE INVENTION

The present inventors have carried out intensive studies and surprisingly found that, in the synthesis step of the molecular sieve, after the preparation of a crystallized mother liquor, an appropriate post-treatment step may produce a molecular sieve having a high proportion of mesopores and a large mesopore surface area. Thus, a molecular sieve having high mesopore volume and high mesopore surface area is prepared and thus the present invention is completed. And, one closed hysteresis loop appears in the range of $P/P_0$=0.4-0.99 in the low temperature nitrogen gas adsorption-desorption curve of the molecular sieve of the present invention, and the starting location of the closed hysteresis loop is in the range of $P/P_0$=0.4-0.6. The catalytic activity of the catalyst prepared with the molecular sieve is greatly improved. In addition, the present inventors have also found that the catalyst preparation by a specific step can make the catalytic active component disperse on the support in a highly dispersed and good state, so that the activity of the catalyst is further improved while the long life period of the catalyst is maintained.

Specifically speaking, the present invention provides a molecular sieve having mesopores (thereinafter also referred as the molecular sieve of the present invention), which has a chemical composition formula, based on the oxide form: $Al_2O_3.SiO_2.M_2O.Z_xO_y$, wherein said M is at least one selected from alkali metals, Z is at least one selected from Mg, Ca, Zn, Ti, Fe, Ga, Ge, B, P, and rare-earth metals, x represents the atom number of Z and is an integral number of 1-6, y represents the number required for satisfying the oxidation state of Z, in term of the molar ratio, $Al_2O_3:SiO_2:M_2O:Z_xO_y$ is 1:(100-300):(0-100):(0-100).

In the molecular sieve of the present invention, the silica/alumina molar ratio is 100-300. One closed hysteresis loop appears in the range of $P/P_0$=0.4-0.99 in the low temperature nitrogen gas adsorption-desorption curve of the molecular sieve of the present invention, and the starting location of the closed hysteresis loop is in the range of $P/P_0$=0.4-0.6, more preferably the starting location is in the range of $P/P_0$=0.4-0.55.

In case that the molecular sieve of the present invention is characterized by the nitrogen gas adsorption BET (Brunner Emmet Teller) method, said molecular sieve has a mesopore surface area of 30 $m^2/g$-280 $m^2/g$, preferably 50 $m^2/g$-250 $m^2/g$, more preferably 80 $m^2/g$-200 $m^2/g$, further preferably 100 $m^2/g$-180 $m^2/g$, further preferably 120 $m^2/g$-150 $m^2/g$.

In case that the molecular sieve of the present invention is characterized by the nitrogen gas adsorption BET (Brunner Emmet Teller) method, said molecular sieve has a specific surface area of 150 $m^2/g$-400 $m^2/g$, preferably 180 $m^2/g$-350 $m^2/g$, more preferably 200 $m^2/g$-320 $m^2/g$, further more preferably 240 $m^2/g$-300 $m^2/g$, further more preferably 260 $m^2/g$-280 $m^2/g$.

The ratio of the mesopore surface area to the molecular sieve surface area of the molecular sieve of the present invention is 20%-70%, preferably 25%-65%, more preferably 28%-60%, more preferably 30%-55%, more preferably 35%-50%.

The molecular sieve of the present invention may be a 10-membered ring aluminosilicate molecular sieve having mesopores or a 12-membered ring aluminosilicate molecular sieve having mesopores.

The molecular sieve of the present invention may be at least one selected from ZSM-11, ZSM-22, ZSM-23, ZSM-35, ZSM-48, ZSM-57, Nu-10, Nu-13, Nu-87, EU-1, EU-13, ITQ-13, ZSM-12 and Beta molecular sieve, preferably ZSM-22 or Beta molecular sieve.

The present invention also provides an aqueous molecular sieve precursor, which has a chemical composition formula of $Al_2O_3.SiO_2.M_2O.Z_xO_y$•templet agent•water, wherein said M, Z, x, and y are as defined above, the molar ratio of $Al_2O_3$ to $SiO_2$ is 1:(20-100), the molar ratio of $Al_2O_3$ to $M_2O$ is 1:(0-100), the molar ratio of $Al_2O_3$ to $Z_xO_y$ is 1:(0-100), the molar ratio of $Al_2O_3$ to the templet agent is 1:(0.001-10), the dry basis content of said aqueous molecular sieve precursor is 5 wt %-30 wt %, preferably 6 wt %-15 wt %.

The present invention also provides a process for preparing a molecular sieve having mesopores, wherein said process comprises the following steps:

mother liquor preparation step, wherein a mixture containing an alumina source, a silica source, a templet agent, an optional alkali metal oxide source, optionally a third oxide source and water (hereinafter referred as the mixture) is crystallized under a crystallization condition to produce a crystallized mother liquor;

filtration step, wherein the crystallized mother liquor is filtered to produce a filter cake having a dry basis content of 5 wt %-30 wt %;

precursor preparation step, wherein said filter cake is directly calcined to produce a molecular sieve precursor;

hydrothermal treatment step, wherein said molecular sieve precursor is subjected to the hydrothermal treatment; and finished product preparation step, wherein the hydrothermally treated product is filtered, optionally washed, dried, and further calcined.

The present invention also provides a process for preparing an aqueous molecular sieve precursor, wherein said process comprises the following steps:

mother liquor preparation step, wherein a mixture containing an alumina source, a silica source, a templet agent, an optional alkali metal oxide source, optionally a third oxide source and water (hereinafter referred as the mixture) is crystallized under a crystallization condition to produce a crystallized mother liquor;

aqueous molecular sieve precursor preparation step, wherein the crystallized mother liquor is filted to produce an aqueous molecular sieve precursor, wherein the dry basis content of said aqueous molecular sieve precursor is 5 wt %-30 wt %, preferably 6 wt %-15 wt %.

The present invention also provides a catalyst, which contains a support and an active metal component supported on said support. In the catalyst of the present invention, said active metal component is on the molecular sieve in a highly dispersed state. Specifically, the single particle of said active metal component has a size of less than 3 nm, for example 0.1-2.8 nm.

The present invention also provides a process for preparing a catalyst, wherein said process comprises the following steps:

(I) an active metal component precursor and an organic complexing agent are supported on a support through impregnation, and the resulting material is optionally dried and calcined to produce a semi-finished catalyst; and (II) the semi-finished catalyst obtained in step (I) is impregnated by using a solution containing an organic complexing agent as impregnation solution, and then dried.

The present invention provides a hydroisomerization catalyst, wherein at least one active metal component selected from Group VIII noble metals is supported on the molecular sieve of the present invention.

The present invention provides a hydroisomerization process, wherein the hydroisomerization catalyst of the present invention is used.

TECHNICAL EFFECT

According to the molecular sieve having mesopores of the present invention, the molecular sieve has the reduced proportions of the volume and the surface area of micropores and the increased proportions of the volume and the surface area of mesopores, and during the reaction using said molecular sieve, the reactants are prone to come into mesopores of the molecular sieve, and further due to the increased mesopore surface area, the molecular sieve can provide more reactive sites in the pore channels. Thus, the catalyst by using the molecular sieve of the present invention as the support can greatly enhance the catalytic efficiency of the catalyst and improve the physical properties of the resulting product.

The treatment of the feedstock oil with the hydroisomerization catalyst of the present invention can achieve an excellent effect of isomerization to reduce the freezing point.

In addition, by the process for preparing the catalyst of the present invention, the life of the catalyst is greatly improved, and the active metals as the catalytic site are highly distributed in a high dispersion on the support, thereby further improving the activity of the catalyst.

DETAILED DESCRIPTION OF THE INVENTION

Figure 1:
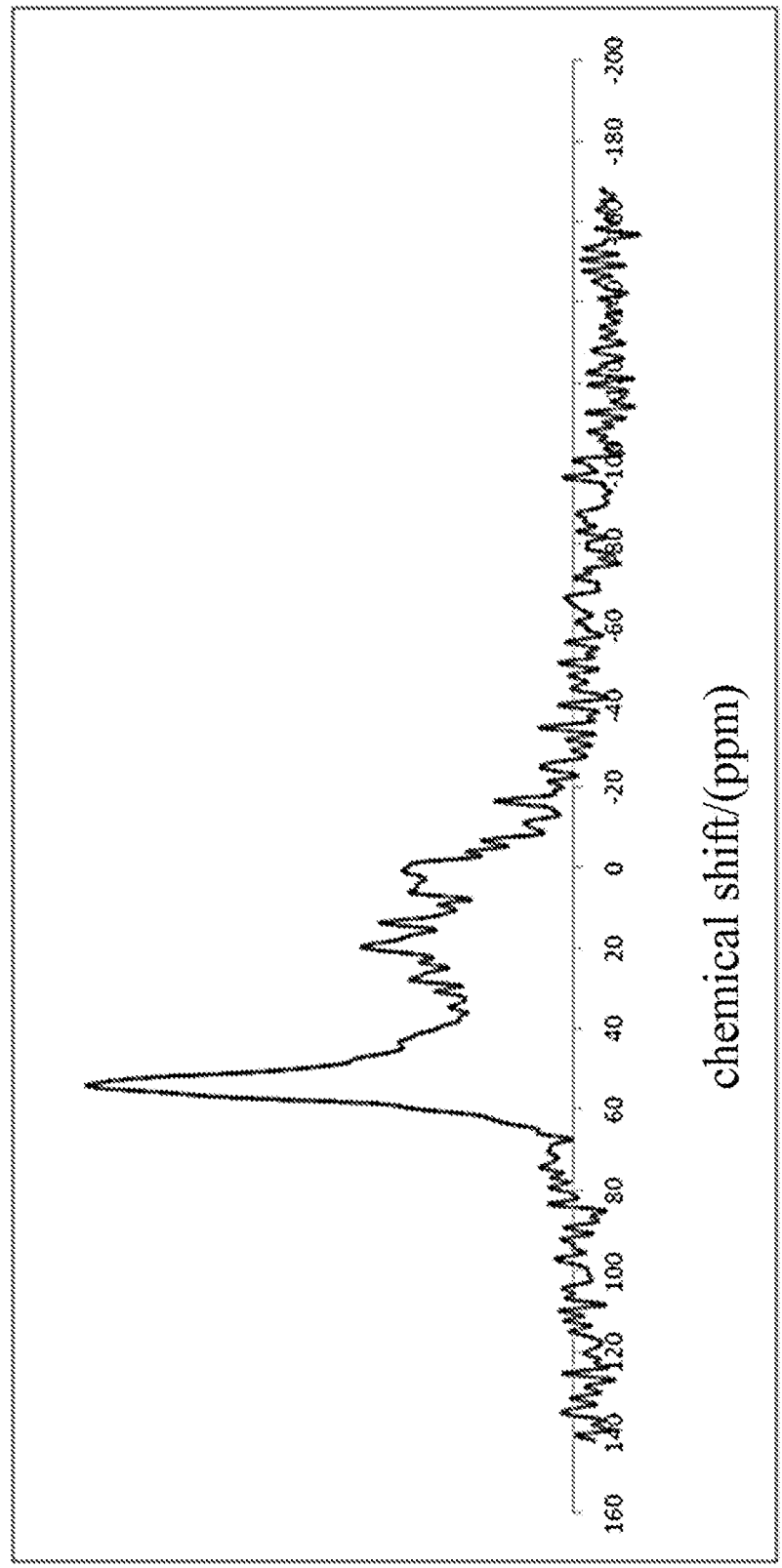
FIG. 1 is a $^{27}$Al NMR spectrum of the molecular sieve precursor C-1-1 prepared in Example 1-1.

Hereinafter, embodiments of the present invention will be described in detail, however, it should be noted that the protection scope of the present invention is not limited to these specific embodiments, but rather defined by the appended claims.

All publications, patent applications, patents, and other references mentioned in this specification are all incorporated herein by reference. Unless otherwise defined, all technical and scientific terms used in this specification have the same meanings as commonly understood by those skilled in the art. In the event of any conflict, the definition in this specification shall prevail.

When a material, a substance, a method, a step, a plant, a component or the like is derived by an expression/prefix such as "well known to those skilled in the art", "prior art", or the like in the specification, the object derived by the expression/prefix covers not only those conventionally used in the art at the time of filing this application, but also those that are not currently commonly used, but will become known in the art to be suitable for the similar purpose.

In the context of this specification, except for what is explicitly stated, any item or matter not mentioned is directly applicable to those known in the art without any changes. Moreover, any of the embodiment(s) described herein may be freely combined with one or more other embodiment(s) described herein, and the resulting technical solutions or technical ideas are regarded as part of the original disclosure or the original record of the present invention, and should not be regarded as new content that has not been disclosed or anticipated in this specification, unless those skilled in the art believe that the combination is obviously unreasonable.

In the context of the present invention, unless clearly defined otherwise, or the meaning is beyond the understanding of those skilled in the art, the hydrocarbon or the hydrocarbon derivative group having 3 or more carbon atoms (such as propyl, propoxy, butyl, butane, butene, butenyl, hexane, etc.) that is not preceded by the prefix "n-" has the same meaning as those preceded by the prefix "n-". For example, propyl is generally understood as n-propyl, and butyl is generally understood as n-butyl. In addition, in the present invention, the number following the carbon atom represents the number of carbon atoms, and for example, C2-C7 means that the number of carbon atoms is 2-7. When used in a compound, it means the number of carbon atoms contained in the compound, for example, C2-C7 carboxylic acid means a carboxylic acid having 2-7 carbon atoms.

In the context of the present specification, with respect to the molecular sieve, before those substances other than water and metal ions filled in pore-channels upon the synthesis of the molecular sieve (for example the template agent molecule and the like) in its pore-channels are removed, it is named "aqueous molecular sieve precursor". In the present invention, the intermediate derived from calcining the filter cake obtained from the crystallized mother liquor is named "the (molecular sieve) precursor".

In the context of the present specification, the structure of the molecular sieve is determined by the X-ray diffraction (XRD) spectrum. The X-ray diffraction (XRD) spectrum is measured with an X-ray powder diffractometer by using a Cu-Kα ray source and a nickel filter. Before testing the sample, the crystallization of the sample of the molecular sieve is observed with a scanning electron microscope (SEM) to confirm that only one crystal is contained in the sample, that is to say, the sample of the molecular sieve is in a pure phase; and then based on that, the XRD test is carried out, so that it is guaranteed that no interference peak of other crystals is present in the diffraction peaks of the XRD spectrum.

In the context of the present specification, the specific surface area is the total area per unit mass of the sample, including an internal surface area and an external surface area. Non-porous samples such as Portland cement and some clay mineral powders/particles only have the external surface area; while the porous samples such as asbestos fiber, diatomaceous earth and the molecular sieve have the external surface area and the internal surface area. The specific surface area in the present invention is measured by using the BET method known in the art.

In the context of the present specification, the mesopore refers to the pore-channels having a pore diameter of 2-50 nm in the molecular sieve; and the mesopore surface area refers to the surface area of the pore-channels having a pore diameter of 2-50 nm. The mesopore surface area of the present invention is obtained by the BET method through the calculation using the BET equation and the t-plot equation.

In the present invention, "dry basis content" is defined as the percentage of the material mass after calcining the material at 600° C. for 4 hours in the air atmosphere relative to the material mass before the calcination.

In the context of the present invention, unless otherwise specified, the physical property values (such as boiling point) of the material are the values measured at room temperature (25° C.) and normal pressure (101325 Pa).

The present invention relates to a molecular sieve having mesopores. The molecular sieve of the present invention have mesopores that are not possessed by the molecular sieves synthesized according to the prior art. And, the molecular sieve of the present invention satisfies the following condition: one closed hysteresis loop appears in the range of $P/P_0=0.4-0.99$ between the adsorption branch and the desorption branch on the low temperature nitrogen gas adsorption-desorption curve, and the starting location of the closed hysteresis loop is in the range of $P/P_0=0.4-0.7$.

Specifically speaking, the present invention provides a molecular sieve having mesopores, which has a chemical composition formula, based on the oxide form: $Al_2O_3 \cdot SiO_2 \cdot M_2P \cdot Z_xO_y$, wherein said M is at least one selected from alkali metals, Z is at least one selected from Mg, Ca, Zn, Ti, Fe, Ga, Ge, B, P, and rare-earth metals, x represents the atom number of Z and is an integral number of 1-6, y represents the number required for satisfying the oxidation state of Z, in term of molar ratio, $Al_2O_3:SiO_2:M_2O:Z_xO_y$ is 1:(100-300):(0-100):(0-100).

It is known that the molecular sieve sometimes (especially immediately after preparation) contains a certain amount of water, but it is believed according to the present invention that it is not necessary to limit the amount of water, because the water is usually kind of channel water, which will not substantially affect the composition of the molecular sieve and its XRD spectrum. In view of this, the chemical composition of the present invention actually represents the anhydrous chemical composition of the molecular sieve.

In the prior art, the silica/alumina ($SiO_2/Al_2O_3$) molar ratio (the silica-alumina ratio) of the molecular sieve is typically less than 100. However, the silica/alumina ($SiO_2/Al_2O_3$) molar ratio of the molecular sieve having mesopores of the present invention is 100-300. In particular, the silica/alumina molar ratio may be for example 110, 120, 130, 140, 150, 160, 170, 180, 190, 200, 210, 220, 230, 240, 250, 260, 270, 280, 290, 300 and any value range formed by any two of these point values. In a preferred embodiment of the present invention, the silica/alumina molar ratio of said molecular sieve having mesopores is preferably 120-260, more preferably 150-200.

The molecular sieve having mesopores of the present invention, as oxide, besides alumina and silica, may also optionally contain at least one alkali metal oxide ($M_2O$), for example, lithium oxide, sodium oxide, potassium oxide, rubidium oxide, cesium oxide. In the molecular sieve of the present invention, the molar ratio of said alkali metal oxide relative to $Al_2O_3$ is 0-100, for example 0.01-80, 0.05-60, 0.1-40, or 1-20. In addition, the molar ratio of said alkali metal oxide relative to $Al_2O_3$ may be 0.005, 0.01, 0.03, 0.05, 0.08, 0.1, 0.3, 0.5, 0.8, 1, 5, 10, 15, 25, 30, 35, 45, 50, 55, 65, 70, 75, 80 and any value range formed by any two of these point values. In an embodiment of the present invention, in the molecular sieve, the molar ratio of said alkali metal oxide is 0 (i.e. free of alkali metal oxide). In an embodiment of the present invention, in the molecular sieve, the molar ratio of said alkali metal oxide is 1-50. In case that the molecular sieve of the present invention contains two or more alkali metal oxides, said molar ratio is based on the total of all of alkali metal oxides.

The molecular sieve of the present invention, as oxide, may also optionally contain at least one oxide of the element ($Z_xO_y$, thereinafter also referred as a third oxide) selected from Mg, Ca, Zn, Ti, Fe, Ga, Ge, B, P, and rare-earth metals, wherein x represents the atom number of Z, and is an integral number of 1-6, y represents the number required for satisfying the oxidation state of Z, x is preferably 1, 2, 3 or 4. In the molecular sieve, the molar ratio of at least one oxide of the element selected from Mg, Ca, Zn, Ti, Fe, Ga, Ge, B, P, and rare-earth metals relative to $Al_2O_3$ is 0-100, for example 0.01-80, 0.05-60, 0.1-40, or 1-20. In addition, the molar ratio of said third oxide relative to $Al_2O_3$ may be 0.005, 0.01, 0.03, 0.05, 0.08, 0.1, 0.3, 0.5, 0.8, 1, 5, 10, 15, 25, 30, 35, 45, 50, 55, 65, 70, 75, 80 and any value range formed by any two of these point values. In an embodiment of the present invention, in the molecular sieve, the molar ratio of said third oxide is 0 (i.e. free of third oxide). In an embodiment of the present invention, in the molecular sieve, the molar ratio of said third oxide is 3-50. In case that the molecular sieve of the present invention contains two or more third oxides, said molar ratio is based on the total of all of third oxides.

In an embodiment of the present invention, in case that the molecular sieve having mesopores is characterized by the nitrogen gas adsorption BET (Brunner Emmet Teller) method, said molecular sieve has a mesopore surface area of 30 $m^2/g$-280 $m^2/g$, preferably 50 $m^2/g$-250 $m^2/g$, more preferably 80 $m^2/g$-200 $m^2/g$, further preferably 100 $m^2/g$-180 $m^2/g$, further preferably 120 $m^2/g$-150 $m^2/g$.

In an embodiment of the present invention, in case that the molecular sieve having mesopores is characterized by the nitrogen gas adsorption BET (Brunner Emmet Teller) method, said molecular sieve may have a specific surface area of 150 $m^2/g$-400 $m^2/g$, preferably 180 $m^2/g$-350 $m^2/g$, more preferably 200 $m^2/g$-320 $m^2/g$, further more preferably 240 $m^2/g$-300 $m^2/g$, further more preferably 260 $m^2/g$-280 $m^2/g$.

In an embodiment of the present invention, the molecular sieve having mesopores may have a ratio of said mesopore surface area to the specific surface area of the molecular sieve of 20%-70%, preferably 25%-65%, more preferably 28%-60%, more preferably 30%-55%, more preferably 35%-50%.

The molecular sieve having mesopores of the present invention comprises a mesopore structure. According to the provision of International Union of Pure and Applied Chemistry (IUPAC), the standard definition of the mesopore is the pore diameter of 2-50 nm. According to the molecular sieve of the present invention, the pore diameter of the mesopore is within said numerical range, however, it does not necessarily mean that the lower limit of the mesopore of the present invention must reach 2 nm, and/or the upper limit of the mesopore must reach 50 nm. The molecular sieve of the present invention having mesopores means, as stated above, the ratio of the mesopore surface area to the molecular sieve surface area may be 20%-70%, preferably 25%-65%, more preferably 28%-60%, more preferably 30%-55%, more preferably 35%-50%.

The molecular sieve having mesopores according to the present invention satisfies the following condition: one closed hysteresis loop appears in the range of $P/P_0=0.4$-0.99 between the adsorption branch and the desorption branch on the low temperature nitrogen gas adsorption-desorption curve, and the starting location of the closed hysteresis loop is in the range of $P/P_0=0.4$-0.7. In contrast, the molecular sieve prepared in the prior art does not have this feature, i.e. there is no hysteresis loop in said range, or the starting location of the hysteresis loop appears at a higher partial pressure (usually $P/P_0>0.7$). In an embodiment of the present invention, the starting location of the closed hysteresis loop is preferably in the range of $P/P_0=0.4$-0.6, more preferably the starting location is in the range of $P/P_0=0.4$-0.55.

The precursor of the molecular sieve having mesopores of the present invention is rich in the penta-coordinated aluminium, while the content of the penta-coordinated aluminium in the molecular sieve product is very low. Specifically, in an embodiment of the present invention, in said precursor of the molecular sieve having mesopores, the content of the penta-coordinated aluminium is 4%-35%, preferably 10%-30%, more preferably 15%-25%. In an embodiment of the present invention, the content of the penta-coordinated aluminium in the molecular sieve product is 5% or less, preferably 3% or less, more preferably 2% or less, further preferably 1% or less. In an embodiment of the present invention, the molecular sieve product is substantially free of the penta-coordinated aluminium.

In an embodiment of the present invention, the molecular sieve having mesopores of the present invention is a 10-membered ring aluminosilicate molecular sieve having mesopores or a 12-membered ring aluminosilicate molecular sieve having mesopores. More specifically, as 10-membered ring molecular sieve, it may be at least one of ZSM-11, ZSM-22, ZSM-23, ZSM-35, ZSM-48, ZSM-57, Nu-10, Nu-13, Nu-87, EU-1, EU-13 and ITQ-13, preferably ZSM-22. As 12-membered ring molecular sieve, it may be Beta molecular sieve, or ZSM-12.

The present invention also provides an aqueous molecular sieve precursor, which has a chemical composition formula of $Al_2O_3 \cdot SiO_2 \cdot M_2O \cdot Z_xO_y \cdot$templet agent$\cdot$water, wherein said M, Z, x, and y are as defined above, the molar ratio of $Al_2O_3$ to $SiO_2$ is 1:(20-100), preferably 1:(25-90), more preferably 1:(30-80). The molar ratio of $Al_2O_3$ to $M_2O$ is 1:(0-100), preferably 1:(0.001-90), more preferably 1:(0.05-80), more preferably 1:(0.1-70), further preferably 1:(0.5-60), further more preferably 1:(1-50). The molar ratio of $Al_2O_3$ to $Z_xO_y$ is 1:(0-100), preferably 1:(0.001-90), more preferably 1:(0.05-80), further preferably 1:(0.1-70), further preferably 1:(0.5-60), further more preferably 1:(1-50). The molar ratio of $Al_2O_3$ to the templet agent is 1:(0.001-10), preferably 1:(0.005-5), more preferably 1:(0.01-4), more preferably 1:(0.05-3), further preferably 1:(0.1-2), further preferably 1:(0.5-1.5), further more preferably 1:(0.8-1).

The dry basis content of said aqueous molecular sieve precursor is 5 wt %-30 wt %. The dry basis content of said aqueous molecular sieve precursor may be 6 wt %, 7 wt %, 8 wt %, 10 wt %, 11 wt %, 12 wt %, 14 wt %, 15 wt %, 17 wt %, 18 wt %, 20 wt %, 22 wt %, 25 wt %, 27 wt % and any value range formed by any two of these point values. The dry basis content of said aqueous molecular sieve precursor is preferably 6 wt %-15 wt %.

In the aqueous molecular sieve precursor of the present invention, the template agent can be the following template agents of the present invention.

The molecular sieve having mesopores of the present invention is prepared through the following preparation process. Based on that, the present invention also provides a process for preparing a molecular sieve having mesopores, wherein said process comprises the following steps: a step in which a mixture containing an alumina source, a silica source, a template agent, an optional alkali metal oxide source, optionally a third oxide source and water (hereinafter referred as the mixture) is crystallized under a crystallization condition to produce a crystallized mother liquor (thereinafter also referred as mother liquor preparation step); a step in which the crystallized mother liquor is filtered to produce a filter cake having a dry basis content of 5 wt %-30 wt % (thereinafter also referred as filtration step); a step in which said filter cake is directly calcined to produce the molecular sieve precursor (thereinafter also referred as precursor preparation step); a step in which said molecular sieve precursor is subjected to the hydrothermal treatment (thereinafter also referred as hydrothermal treatment step); and a step in which the hydrothermally treated product is filtered, optionally washed and dried, and further calcined (thereinafter also referred as finished product preparation step).

In the present invention, the mother liquor preparation step is performed according to the process for preparing the crystallized mother liquor conventionally used in the art. The mother liquor preparation step is changed according to the type of the molecular sieve to be prepared. For example, in the case of Beta molecular sieve, the process for preparing the crystallized mother liquor can refer to those disclosed in U.S. Patent Application U.S. Pat. No. 5,200,168. In the case of ZSM-22 molecular sieve, the process for preparing the crystallized mother liquor can refer to those disclosed in the literature O. Muraza et al., Microporous and Mesoporous Materials 206 (2015) 136-143. In the case of ZSM-48 molecular sieve, the process for preparing the crystallized mother liquor can refer to those disclosed in the literature P. Me'riaudeau et al/Journal of Catalysis, 1999(185), 435-444, or those disclosed in U.S. Patent Application U.S. Pat. No. 5,961,951.

In an embodiment of the present invention, the mother liquor preparation step may be performed by: preparing a mixture of a silicon source-containing solution, an aluminum source-containing solution, an optional alkaline solution (an alkali metal source solution), and optionally a third oxide source solution, gelatinizing the above liquid mixture, and then crystallizing. In an embodiment of the present invention, the mother liquor preparation step may be performed by: adding a silicon source, an aluminum source, an optional alkali metal source, optionally a third oxide source to a solvent, gelatinizing the obtained solution, and then crystallizing.

In one exemplary embodiment of the present invention, the mother liquor preparation step may be performed by: dissolving an alumina source, a template agent and an optional alkali metal oxide source in water to formulate an original solution; optionally activating the above original solution at 50-160° C. (preferably 60-150° C., more preferably 90-140° C., further preferably 95-130° C.) for 2-24 hours (preferably 4-22 hours, more preferably 6-20 hours, further preferably 8-18 hours) to obtain a mixed solution. In the case that the alumina source, the template agent and the optional alkali metal oxide source are soluble in water, the mixed solution may be prepared without the above thermal activation. Then, a silica source, an optional third oxide source and the above mixed solution are mixed and stirred; the resulting slurry is maintained for crystallization at same temperature of 120-180° C. (preferably 130-170° C., more preferably 140-160° C., further preferably 145-155° C.) for 24-150 hours (preferably 30-130 hours, more preferably 35-120 hours, further preferably 40-100 hours, further preferably 50-80 hours) to produce a crystallized mother liquor.

In the mother liquor preparation step, the molar ratio of raw materials as oxide is as follows: $SiO_2/Al_2O_3$=5-600, preferably 10-550, more preferably 20-500, more preferably 50-450, further preferably 60-400, still further preferably 80-300; alkali metal oxide/$Al_2O_3$=0-100, preferably 0.01-90, more preferably 0.1-80, further preferably 0.5-70, further preferably 1-60, further more preferably 2-50; third oxide/$Al_2O_3$=0-100, preferably 0.01-90, more preferably 0.1-80, further preferably 0.5-70, further preferably 1-60, further more preferably 2-50; template agent/$Al_2O_3$=0.001-8, preferably 0.01-6, more preferably 0.02-5, more preferably 0.1-4, further preferably 0.2-3, further preferably 0.5-2, further more preferably 0.8-1.5; $H_2O/Al_2O_3$=4-5000, preferably 10-4000, more preferably 70-3000, further preferably 100-2500, further preferably 150-2000, further more preferably 200-1500. The condition for preparing the crystallized mother liquor is not particularly limited, as long as the crystallized mother liquor for preparing the molecular sieve of the present invention can be produced.

According to the present invention, in the preparation of the crystallized mother liquor, as the silica source, for example, silicic acid, silica gel, silica sol, tetraalkyl silicate ester or water glass and the like may be exemplified. These silica sources may be used alone or in combination at a required ratio.

According to the present invention, in the preparation of the crystallized mother liquor, as the alumina source, for example, aluminium hydroxide, sodium aluminate, aluminium salt, aluminium alkoxide, kaolin or montmorillonite, aluminium sulfate, aluminium nitrate, aluminium carbonate, aluminium phosphate, aluminium chloride, alum, aluminium isopropoxide, aluminium ethoxide, aluminium butoxide and the like may be exemplified.

According to the present invention, in the preparation of the crystallized mother liquor, as the third oxide source, any corresponding oxide source conventionally used in the art for this purpose may be used, including but not limited to an oxide, an alkoxide, an oxometallate, an acetate, an oxalate, an ammonium salt, a sulfate and a nitrate of the corresponding metal in the third oxide. For example for the magnesium source, magnesium sulfate, magnesium chloride, magnesium nitrate, magnesium gluconate and the like may be exemplified. For example for the calcium source, calcium hydroxide, calcium sulfate, calcium chloride, calcium nitrate and the like may be exemplified. As the zinc source, zinc sulfate, zinc chloride, zinc nitrate and the like may be exemplified. As the titanium source, titanium tetraalkoxide, titanium oxide, titanium nitrate and the like may be exemplified. As the iron source, iron chloride, ferric nitrate, and ferric sulfate may be exemplified. As the gallium source, for example, gallium nitrate, gallium sulphate, gallium oxide and the like may be exemplified. As the germanium source, for example germanium tetraalkoxide, germanium oxide, germanium nitrate and the like may be exemplified. As the boron source, boric acid, borate, borax, boron trioxide and the like may be exemplified. As the phosphorus source, phosphoric acid, phosphate, and phosphorus pentoxide may be exemplified. As the rare-earth metal source, lanthanum oxide, neodymium oxide, yttrium oxide, cerium oxide, lanthanum nitrate, neodymium nitrate, yttrium nitrate, ammonium cerous sulphate and the like may be exemplified.

According to the present invention, in the preparation of the crystallized mother liquor, as the alkali metal oxide source, an acid salt, acetate, oxalate, ammonium salt, sulfate, nitrate and the like of an alkali metal may be used. Further, as the alkali metal source, alkali metal hydroxide may be used, which also has the function of an alkaline solution.

According to the present invention, in the preparation of the crystallized mother liquor, as the template agent, any templating agent well known to those skilled in the art for the synthesis of the molecular sieve may be used. For example, it may be a template agent conventionally used for the preparation of ZSM-11, ZSM-22, ZSM-23, ZSM-35, ZSM-48, ZSM-57, Nu-10, Nu-13, Nu-87, EU-1, EU-13, ITQ-13, ZSM-12 and Beta molecular sieves.

In the present invention, the template agents that may be used include an amine compound, a quaternary phosphonium compound and a quaternary ammonium compounds. The latter two may be usually represented by the formula of ($R_4X^+$•counter ion), wherein X is N or P, each R individually represents linear or branched $C_1$-$C_{12}$alkyl, $C_5$-$C_{10}$cycloalkyl, $C_6$-$C_{12}$aryl, $C_1$-$C_{12}$alkyl$C_6$-$C_{12}$aryl, the coordination number of $R_4X^+$ depends on the valence of the counter ion and is for example 1 or 2, the counter ion represents an anion having a valence corresponding to the $R_4X^+$ group, which may be selected from chloride ion, fluoride ion, bromide ion, nitrate radical, sulfate radical, and hydroxide radical. As the template agent, a monoamine, a diamine and a triamine, including a mixed amine, can also be used as the template agent, which may be either a single template agent or a mixture of multiple template agents.

According to the present invention, the representative template agent comprises tetramethyl ammonium salt, tetraethyl ammonium salt, tetrapropyl ammonium salt, tetrabutyl ammonium salt, tetrapentyl ammonium salt di-n-polyamine, tripolyamine, triethylamine, triethanolamine, cyclohexyl amine, dimethylpyridine, diethylpyridine, N,N-dimethyl benzene, N,N-diethanol, dicycloethyl, N,N-dimethylethanolamine, 1,4-diazabicyclo-(2,2,2)octane ion, di-n-butyl amine, neopentyl amine, di-n-pentyl amine, isopropyl amine, tert-butyl amine, pyridine/pyrrolidine and 2-imidazolone, cetyl trimethylammonium bromide, tetramethyl ammonium hydroxide (chloride, bromide, iodide), tetraethyl ammonium hydroxide (chloride, bromide, iodide), tetrapropyl ammonium hydroxide (chloride, bromide, iodide), tetrabutyl ammonium hydroxide (chloride, bromide, iodide), tetrapentyl ammonium hydroxide (chloride, bromide, iodide), however is not limited thereto.

In said filtration step, the crystallized mother liquor is filtered to produce a filter cake having a dry basis content of 5 wt %-30 wt %. The purpose of filtering the crystallized mother liquor is to remove the redundant mother liquor in the syntheses. In the present invention, the filtration condition is controlled so that the dry basis content of the formed filter cake is in a specified range. Specifically, in the present invention, said filter cake has a dry basis content of 5 wt %-30 wt %. In addition, the dry basis content of the filter cake may be 6 wt %, 7 wt %, 8 wt %, 10 wt %, 11 wt %, 12 wt %, 14 wt %, 15 wt %, 17 wt %, 18 wt %, 20 wt %, 22 wt %, 25 wt %, 27 wt % and any value range formed by any two of these point values. The dry basis content of said filter cake is preferably 6 wt %-15 wt %. In case that the dry basis content of the filter cake is beyond the above range, the finally prepared molecular sieve does not satisfy the requirements of the molecular sieve having mesopores of the present invention and its physicochemical properties cannot achieve the object of the present invention.

In said precursor preparation step, the filter cake is directly calcined to obtain a molecular sieve precursor. In this step, the filter cake obtained from the filtration step is directly calcined at a high temperature without drying. In an embodiment of the present invention, said calcination temperature is 300° C.-900° C., preferably 350° C.-800° C., more preferably 400° C.-700° C., further more preferably 450° C.-600° C., further more preferably 450° C.-550° C. In an embodiment of the present invention, the heating rate upon calcination may be 5° C./minute-100° C./minute, preferably 10° C./minute-50° C./minute, more preferably 20° C./minute-40° C./minute, further more preferably 30° C./minute-40° C./minute. In an embodiment of the present invention, the calcination time may be 1 hour-20 hours, preferably 2 hours-16 hours, more preferably 5 hours-15 hours, further more preferably 6 hours-12 hours. The calcination environment may be a natural environment, i.e. an oxygen-containing gas is not purposely introduced upon calcination, or the calcination may also be performed with introducing the oxygen gas, as required. Without wishing to be bound by theory, it has been conjectured by the present inventors that through the calcination, the water remained in the filter cake can oxidate and remove the template agent, and through the calcination in those conditions, the water and the aluminium in the molecular sieve may be interacted to form a non-framework aluminium.

In this way, the product obtained from the precursor preparation step in the present invention (i.e., the molecular sieve precursor) contains a large amount of penta-coordinated non-framework aluminium (i.e., the penta-coordinated aluminium). In an embodiment of the present invention, the molecular sieve precursor has a penta-coordinated aluminium content of 4%-35%, preferably 10%-30%, more preferably 15%-25%, wherein the penta-coordinated non-framework aluminium is defined as the peak at the chemical shift δ of 10-40 ppm in the $^{27}Al$ NMR spectrum. The measuring condition for the $^{27}Al$ NMR spectrum can be found the publications, such as Guoliang Zhao et al, Applied Catalysis A: General 299 (2006) 167-174.

In an embodiment of the present invention, the molecular sieve precursor obtained after the calcination may be naturally cooled to lower the temperature. Preferably, the temperature is lowered to room temperature.

In said hydrothermal treatment step, said molecular sieve precursor is hydrothermally treated. In an embodiment of the present invention, the medium of the hydrothermal treatment is an acidic aqueous solution. According to the present invention, said acidic aqueous solution refers to an $H^+$ containing aqueous solution, wherein water may be tap water, pure water, deionized water or the like. $H^+$ is an ion released from the dissociation of an organic acid and/or an inorganic acid. In an embodiment of the present invention, in order to obtain said acidic aqueous solution, at least one of hydrochloric acid, sulfuric acid, phosphoric acid, nitric acid, citric acid, acetic acid, maleic acid, oxalic acid, aminotriacetic acid, 1,2-cyclohexane diamine tetraacetic acid, tartaric acid and malic acid, preferably hydrochloric acid and/or citric acid may be added to water. In an embodiment of the present invention, the content of the inorganic acid and/or organic acid in said acidic aqueous solution may be 0.01M-5M, preferably 0.05M-2M, more preferably 0.2M-1.5M, further preferably 0.5-1.2M, further more preferably 0.8-1.1M.

In an embodiment of the present invention, in said hydrothermal treatment step, the liquid-solid volume ratio may be 5-200, preferably 20-100, more preferably 40-80, further preferably 50-70.

In an embodiment of the present invention, in said hydrothermal treatment step, the temperature of said hydrothermal treatment may be 80° C.-300° C., preferably 100° C.-200° C., more preferably 120° C.-180° C., further preferably 140° C.-160° C.

In an embodiment of the present invention, in said hydrothermal treatment step, the time of the hydrothermal treatment may be 0.1 hour-24 hours, preferably 0.5 hour-18 hours, more preferably 1 hour-12 hours, more preferably 2 hours-10 hours.

In an embodiment of the present invention, in said hydrothermal treatment step, said hydrothermal treatment may be carried out in an open vessel, or may be also carried out in a closed vessel, preferably carried out in a closed vessel. In an embodiment of the present invention, the pressure of said hydrothermal treatment is an autogenous pressure formed under the hydrothermal condition in a closed vessel.

In said finished product preparation step, the hydrothermally treated product is filtered, optionally washed, and dried. The filtration method is not particularly limited, and may be a method known to those skilled in the art, such as filtration, suction filtration using a Buchner funnel and the like. The washing method is not particularly limited, and water washing may be carried out by using deionized water. In an embodiment of the present invention, water washing can proceed until the pH of the filtrate is 4-8, preferably pH is 6-7. The pH value of the solution may be measured with a pH test paper or a pH meter, and the measurement method is not particularly limited, and may be a method known to those skilled in the art.

In said finished product preparation step, the molecular sieve obtained from the filtration is optionally dried. The drying method is not particularly limited, and may be a method known to those skilled in the art; for example, according to a conventional method, the drying may be carried out at 120° C. for 6 hours. Then, the calcination will further proceed, and said calcination condition is the conventional condition commonly used for the preparation of the molecular sieve in the art, and may be the calcination condition in the above-mentioned precursor preparation step. For example, the calcination may be carried out at 400° C.-600° C. for 2-8 hours.

Thus, the molecular sieve having mesopores of the present invention is obtained.

One closed hysteresis loop appears in the range of P/P0=0.4-0.99 between the adsorption branch and the desorption branch on the low temperature nitrogen gas adsorption-desorption curve of the molecular sieve having mesopores according to the present invention, and the starting location of the closed hysteresis loop is in the range of P/P0=0.4-0.7. In contrast, for the molecular sieve prepared in the prior art, there is no hysteresis loop in said range, or the starting location of the hysteresis loop appears at a higher partial pressure (usually P/P0>0.7). In an embodiment of the present invention, the starting location of the closed hysteresis loop is in the range of P/P0=0.4-0.6, more preferably the starting location is in the range of P/P0=0.4-0.55.

The present invention also provides a process for preparing an aqueous molecular sieve precursor, wherein said process comprises the following steps:

mother liquor preparation step, wherein a mixture (hereinafter referred as the mixture) containing an alumina source, a silica source, a templet agent, an optional alkali metal oxide source, optionally a third oxide source and water is crystallized under a crystallization condition to produce a crystallized mother liquor;

aqueous molecular sieve precursor preparation step, wherein the crystallized mother liquor is filtered to produce an aqueous molecular sieve precursor, wherein the dry basis content of said aqueous molecular sieve precursor is 5 wt %-30 wt %, preferably 6 wt %-15 wt %.

The proportion of each component and the condition in the mother liquor preparation step in the process for preparing the aqueous molecular sieve precursor of the present invention is identical to the proportion of each component and the condition in the mother liquor preparation step in the above-mentioned process for preparing the molecular sieve of the present invention.

The aqueous molecular sieve precursor is prepared by the process for preparing the aqueous molecular sieve precursor of the present invention. The dry basis content of said aqueous molecular sieve precursor is the dry basis content of the filter cake obtained in the above-mentioned filtration step of the present invention. The aqueous molecular sieve precursor may be directly used in the precursor preparation step in the process for preparing the above-mentioned molecular sieve of the present invention.

The molecular sieve having mesopores of the present invention may be directly used as the solid acid catalyst. In addition, in an embodiment of the present invention, an active component may be supported on the molecular sieve having mesopores according to the present invention to prepare a catalyst for use. The catalyst of the present invention formed therefrom has not only a good hydroisomerization activity, but also can produce a product having a low pour point with a high yield.

The present invention also provides a catalyst, which contains a support and an active metal component supported on said support.

In an embodiment of the present invention, said active metal component is at least one selected from Group VIII noble metals. In an embodiment of the present invention, the Group VIII noble metal is preferably at least one selected from ruthenium, osmium, palladium, platinum, rhodium and iridium. In an embodiment of the present invention, said active metal component is a combination of platinum component and palladium component. In an embodiment of the present invention, the molar ratio of Pt component to Pd component is 1:2-10, preferably 1:2-8, further preferably 1:2-6, more preferably 1:2-4.

In an embodiment of the present invention, in the catalyst of the present invention, said active metal component is present on the support in a highly dispersed state. Specifically, the single particle of said active metal component has a size of less than 3 nm, for example 0.1-2.8 nm.

According to the present invention, said active metal component may be provided in form of the active metal component precursor. Said active metal component precursor is preferably selected from a compound containing an element of Group VIII noble metal. As said compound containing an element of Group VIII noble metal, it may be at least one selected from nitrate, chloride, sulfate, formate, acetate, phosphate, citrate, oxalate, carbonate, basic carbonate, hydroxide, phosphate, phosphide, sulfide, aluminate, molybdate, tungstate, complexes of these salts, and water soluble oxides, all of which contain an element of Group VIII noble metal.

In the catalyst of the present invention, based on the total weight of the catalyst, in term of element content, the content of the active metal component may be properly determined as required, and usually may be 0.001 wt %-5 wt %, preferably 0.005 wt %-4.5 wt %, preferably 0.01 wt %-4 wt %, more preferably 0.1 wt %-3 wt %, more preferably 0.2 wt %-1 wt %, still further preferably 0.4 wt %-0.8 wt %.

In the catalyst of the present invention, as said porous support, those organic or inorganic porous solids conventionally used as the support in the preparation of a supported-type catalyst in the art may be exemplified.

Specifically, as said organic porous solid, for example, olefin homopolymer or copolymer, polyvinyl alcohol or a copolymer thereof, cyclodextrin, (co)polyester, (co)polyamide, vinyl chloride homopolymer or copolymer, acrylate homopolymer or copolymer, methacrylate homopolymer or copolymer, styrene homopolymer or copolymer and the like, and a partially crosslinked form of these homopolymers or copolymers, preferably partially crosslinked (for example the crosslinking degree is at least 2% but less than 100%) styrene polymer may be exemplified.

According to an embodiment of the present invention, said organic porous solid is subjected to a thermal activation treatment and/or a chemical activation treatment before use. According to the present invention, said organic porous solid may be only subjected to a thermal activation treatment before use, or may be also only subjected to a chemical activation treatment before use, or may be successively subjected to said thermal activation treatment and said chemical activation treatment in an arbitrary combination sequence before use, and there is no special limitation.

The thermal activation treatment may be carried out according to a usual manner. For example, said organic porous solid is heated under a reduced pressure or in an inert atmosphere. The inert atmosphere herein means that the gas contains a very small amount of the component that may be reacted with said organic porous solid or is free of the component that may be reacted with said organic porous solid. As said inert atmosphere, for example, nitrogen gas atmosphere or noble gas atmosphere, preferably nitrogen gas atmosphere may be exemplified. Since the organic porous solid has poor heat resistance, the thermal activation process should be carried out based on a precondition that it does not damage the structure and basic composition of the organic porous solid itself. Generally, the thermal activation temperature is 50-400° C., preferably 100-250° C., and the thermal activation time is 1-24 hours, preferably 2-12 hours.

After the thermal activation/chemical activation treatment, the organic porous solid needs to be kept under a positive pressure in an inert atmosphere for later use.

As said inorganic porous solid, for example, a refractory oxide of the metal of Group IIA, IIIA, IVA or IVB of the periodic table of elements (for example silicon dioxide (also referred as silica or silica gel), alumina, magnesia, titania, zirconia, thoria or the like), or any refractory composite oxide of these metals (for example silica-alumina, magnesia-alumina, titania-silica, titania-magnesia, titania-alumina and the like), and clay, molecular sieve (for example ZSM-5 and MCM-41), mica, montmorillonite, bentonite and diatomaceous earth and the like may be exemplified. As said inorganic porous solid, an oxide formed by the pyrohydrolysis of a gaseous metal halide or a gaseous silicon compound, for example silica gel obtained by the pyrohydrolysis of silicon tetrachloride, or alumina obtained by the pyrohydrolysis of aluminium trichloride and the like can also be exemplified.

As said inorganic porous solid, it is preferably silicon dioxide, alumina, magnesia, silica-alumina, magnesia-alumina, titania-silica, titanium oxide, molecular sieve and montmorillonite and the like, in particular preferably silicon dioxide and montmorillonite.

According to the present invention, a suitable silicon dioxide may be produced by a conventional process, or may be any commercially available product, for example, Grace 955, Grace 948, Grace SP9-351, Grace SP9-485, Grace SP9-10046, Daysion Syloid 245 and Aerosil1812 available from the Grace company; ES70, ES70X, ES70Y, ES70W, ES757, EP10X and EP11 available from the Ineos company; and CS-2133 and MS-3040 available from the PQ company.

According to an embodiment of the present invention, said inorganic porous solid is subjected to a thermal activation treatment and/or a chemical activation treatment before use.

According to the present invention, said inorganic porous solid may be only subjected to a thermal activation treatment before use, or may be also only subjected to a chemical activation treatment before use, or may be successively subjected to said thermal activation treatment and said chemical activation treatment in an arbitrary combination sequence before use, and there is no special limitation.

The thermal activation treatment may be carried out according to a usual manner. For example, said inorganic porous solid is heated under a reduced pressure or in an inert atmosphere. The inert atmosphere herein means that the gas contains a very small amount of the component that may be reacted with said inorganic porous solid or is free of the component that may be reacted with said inorganic porous solid. As said inert atmosphere, for example, nitrogen gas atmosphere or noble gas atmosphere, preferably nitrogen gas atmosphere may be exemplified. Generally, the thermal activation temperature is 200-800° C., preferably 400-700° C., most preferably 400-650° C., and the heating time is for example 0.5-24 hours, preferably 2-12 hours, most preferably 4-8 hours.

After the thermal activation/chemical activation treatment, the inorganic porous solid needs to be kept under a positive pressure in an inert atmosphere for later use.

In an embodiment of the present invention, said support is the above-mentioned molecular sieve having mesopores of the present invention. More specifically, the molecular sieve having mesopores is a 10-membered ring aluminosilicate molecular sieve having mesopores or a 12-membered ring aluminosilicate molecular sieve having mesopores. As the 10-membered ring molecular sieve, it may be at least one of ZSM-11, ZSM-22, ZSM-23, ZSM-35, ZSM-48, ZSM-57, Nu-10, Nu-13, Nu-87, EU-1, EU-13 and ITQ-13, preferably ZSM-22. As the 12-membered ring molecular sieve, it may be ZSM-12 or Beta molecular sieve. In an embodiment of the present invention, said support is a combination of the above-mentioned molecular sieve having mesopores of the present invention and a support except for the molecular sieve of the present invention.

In an embodiment of the present invention, at least one component selected from Mg, Ca, Zn, Ti, Fe, Ga, Ge, B, P, and rare-earth metals (thereinafter also referred as auxiliary agent component) can further be supported on the support of the above-mentioned present invention. In an embodiment of the present invention, in the catalyst of the present invention, based on the total weight of the catalyst, in term of element content, the content of the auxiliary agent may be properly determined as required, and usually may be 0.001 wt %-5 wt %, preferably 0.005 wt %-4.5 wt %, preferably 0.01 wt %-4 wt %, more preferably 0.1 wt %-3 wt %, more preferably 0.2 wt %-1 wt %, still further preferably 0.4 wt %-0.8 wt %.

The present invention also provides a process for preparing a catalyst, wherein said process comprises the following steps:

(I) an active metal component precursor and an organic complexing agent are supported on a support by impregnation, and the resulting material is optionally dried and calcined to produce a semi-finished catalyst; and (II) the semi-finished catalyst obtained in step (I) is impregnated by using a solution containing an organic complexing agent as impregnation liquor, and then dried.

According to the present invention, the catalyst is prepared via a two-step impregnation method, and the first step impregnation and the second step impregnation are used to introduce the active metal component and the organic complexing agent respectively. The organic complexing agent is added in the first step impregnation, and converted into the carbon by the calcination. Therefore, not only the activity of the catalyst may be increased, but also the high activity of the catalyst may be effectively maintained for a long time so as to greatly increase the life of the catalyst. Without wishing to be bound by theory, it has been conjectured by the present inventors that the reason maybe is because the organic complexing agent is added in the first-step impregnation, the presence of the organic complexing agent prevents the active metal from aggregating on the support during the calcination so that the active metal is dispersed more uniformly on the support; at the same time, the calcination after the first-step impregnation can convert the metal compound into a metal oxide and the organic complexing agent into carbon, so that the binding between the active metal and the support becomes stronger, and the activity and the stability of the catalyst are improved; and the organic complexing agent added in the second-step impregnation covers the catalyst surface, which can effectively prevent the active metal from aggregating in the reduction process and ensure the high dispersity, so as to further improve the activity of the catalyst. Thus, the problem of the uneven distribution of the active metal component on the support is effectively solved by the process for preparing the catalyst of the present invention. Accordingly, the active metal component is present on the support in a highly dispersed state, and therefore the catalytic activity of the catalyst is greatly increased while the life of the catalyst is prolonged.

In the process for preparing the catalyst of the present invention, the organic complexing agent used in step (I) may be at least one selected from an oxygen-containing organic substance, an organic acid and a nitrogen-containing organic substance. In an embodiment of the present invention, said oxygen-containing organic substance may be a dihydric or higher polyol, preferably a polyol having a carbon atom number of 2-6 or an oligomer or polymer thereof, and for example at least one of ethylene glycol, glycerol, polyethylene glycol, diethylene glycol, and butylene glycol may be exemplified. The molecular weight of said polyethylene glycol is preferably 200-1500. In an embodiment of the present invention, said organic acid may be a $C_2$-$C_{15}$ compound containing one or more than one carboxyl groups, and specifically at least one of acetic acid, maleic acid, oxalic acid, aminotriacetic acid, 1,2-cyclohexane diamine tetraacetic acid, citric acid, tartaric acid and malic acid may be exemplified. In an embodiment of the present invention, said nitrogen-containing organic substance may be at least one of an organic amine and an organic ammonium salt. As said organic amine, it is preferably a $C_2$-$C_{10}$ compound containing one or more than one amino groups, and may be a primary amine, a secondary amine or a tertiary amine, in particular preferably ethylene diamine. As said organic ammonium salt, it is preferably EDTA. Preferably, the organic complexing agent in step (I) is at least one selected from organic acids, more preferably, the organic complexing agent in step (I) is at least one selected from $C_2$-$C_{15}$ fatty acids. A catalyst having a higher activity may be obtained by using an organic acid as the organic complexing agent in step (I).

In step (I), the molar ratio of said organic complexing agent to said active metal component precursor may be 2-100:1, preferably 4-80:1, more preferably 6-70:1, further preferably 10-50:1.

In step (I), the impregnation may be carried out by the impregnation method well known in the art. The temperature of the impregnation liquor during impregnation is not particularly limited, and may be any temperatures which the impregnation liquor can reach. The impregnation time is not particularly limited, and it may be such a time as long as the required component can be supported in desired amount. For example, the impregnation temperature is not particularly limited and may be 15-60° C. The impregnation time is not particularly limited and may be 0.5-5 hours. Upon impregnation, the mass ratio of the liquid containing an organic complexing agent to the support is not particularly limited and may be 0.6:1-2:1, preferably 0.8:1-1.4:1.

In step (I), the condition of the drying is not particularly limited and may be any drying conditions well known in the art. Preferably, in step (I), the drying temperature is 100-250° C., and the drying time is 1-12 hours.

In step (I), preferably, said calcination is carried out in such a condition that based on the total amount of the semi-finished catalyst, the carbon content of the semi-finished catalyst may be 0.05 wt %-0.5 wt %, preferably 0.1 wt %-0.4 wt %. According to the present invention, the above-mention carbon content may be obtained by controlling the calcination temperature in the calcination condition and the introduction amount of the combustion-supporting gas, and said combustion-supporting gas may be various gases having an oxygen content of not less than 20 vol %, and for example may be at least one of air, oxygen and a mixed gas thereof.

In an embodiment of the present invention, the introduction amount of the combustion-supporting gas is not less than 0.2 litre/gram·hour. The introduction of said combustion-supporting gas, on one hand, satisfies the combustion conditions so that the active metal component precursor is converted into the active metal oxide and the organic complexing agent is converted into carbon; and on the other hand can also discharge off carbon dioxide, water and other components formed from the combustion, so as to avoid the hindrance to the vacant sites of the active phase due to the deposition on the catalyst. In an embodiment of the present invention, the introduction amount of the combustion-supporting gas is 0.2-20 litre/(gram·hour), preferably 0.3-10 litre/(gram·hour). The term "gram" herein refers to the weight of the treated support.

In step (I), said calcination temperature may be 350-500° C., preferably 360-450° C. The calcination time may be 0.5-8 hours, preferably 1-6 hours. Controlling the calcination temperature within the above range can ensure the formation of carbon from the organic complexing agent on the support in the above-mentioned content to produce a semi-finished catalyst.

In step (I), relative to the weight of the support to be impregnated, in term of element content, the amount of the active metal component precursor may be properly determined as required, and usually may be 0.001 wt %-5 wt %, preferably 0.005 wt %-4.5 wt %, preferably 0.01 wt %-4 wt %, more preferably 0.1 wt %-3 wt %, more preferably 0.2 wt %-1 wt %, still further preferably 0.4 wt %-0.8 wt %.

In step (I), the used active metal component precursor may be the active metal component precursor in the catalyst of the above-mentioned present invention.

In step (I), the used support may be the above-mentioned support used in the catalyst of the present invention. In an embodiment of the present invention, the support in step (I) is preferably the above-mentioned molecular sieve having mesopores of the present invention. More specifically, the molecular sieve having mesopores is a 10-membered ring aluminosilicate molecular sieve having mesopores or a 12-membered ring aluminosilicate molecular sieve having mesopores. As the 10-membered ring molecular sieve, it may be at least one of ZSM-11, ZSM-22, ZSM-23, ZSM-35, ZSM-48, ZSM-57, Nu-10, Nu-13, Nu-87, EU-1, EU-13 and ITQ-13, preferably ZSM-22. As the 12-membered ring molecular sieve, it may be ZSM-12 or Beta molecular sieve. In an embodiment of the present invention, the support in step (I) is a combination of the above-mentioned molecular sieve having mesopores of the present invention and a support except for the molecular sieve of the present invention.

In step (II), the choice range of the used organic complexing agent is identical to that in step (I). The organic complexing agent used in step (II) may be identical to or different from the organic complexing agent used in step (I).

The molar ratio of the organic complexing agent to the active metal used in step (II) may be 2-100:1, preferably 4-80:1, more preferably 6-70:1, further preferably 10-50:1. Specifically, the molar ratio may be identical to or different from that in step (I).

The impregnation condition and the drying conditions used in step (II) may be those well known in the art. Specifically, the impregnation condition and the drying conditions used in step (II) may be identical to those in step (I).

In the process according to the present invention, the catalyst obtained after drying in step (II) does not need a further calcination. Alternatively, a further calcination may be carried out as required. Said calcination temperature is not particularly limited and may be 350-500° C., preferably 360-450° C. The calcination time is not particularly limited and may be 0.5-8 hours, preferably 1-6 hours.

In an embodiment of the present invention, the process for preparing the catalyst may further comprise a step of reducing the catalyst obtained in step (II). The reducing condition may be any reducing condition well known in the art. Usually, the reducing atmosphere is hydrogen gas, the reduction temperature may be 300-500° C., and the reduction time may be 2-6 hours.

In an embodiment of the present invention, the process for preparing the catalyst may further comprises a step of impregnation with a solution of at least one metal ion derived from Mg, Ca, Zn, Ti, Fe, Ga, Ge, B, P, and rare-earth metals by impregnation. The impregnation may be carried out in step (I) to produce a semi-finished catalyst supported an active metal component and an auxiliary agent component. The impregnation may also be carried out in step (II) to produce a catalyst supported an active metal component and an auxiliary agent component. In addition, this impregnation step may also be carried out before step (I), between step (I) and step (II), or after step (II). In an embodiment of the present invention, preferably this impregnation step is carried out before step (I), during step (I), or between step (I) and step (II). The impregnation condition is not particularly limited, and the above-mentioned impregnation condition of the present invention may be used. Relative to the weight of the support to be impregnated, in term of element, the amount of the auxiliary agent component may be properly determined as required, and usually may be 0.001 wt %-5 wt %, preferably 0.005 wt %-4.5 wt %, preferably 0.01 wt %-4 wt %, more preferably 0.1 wt %-3 wt %, more preferably 0.2 wt %-1 wt %, still further preferably 0.4 wt %-0.8 wt %.

In an embodiment of the present invention, the catalyst of the present invention may be a hydroisomerization catalyst. In an embodiment of the present invention, in the hydroisomerization catalyst, one of Group VIII noble metals is supported on the molecular sieve having mesopores of the present invention as the support. In an embodiment of the present invention, in the hydroisomerization catalyst, two or more of Group VIII noble metals are supported on the molecular sieve having mesopores of the present invention as the support. In an embodiment of the present invention, said hydroisomerization catalyst is the above-mentioned catalyst of the present invention.

The present invention also provides a hydroisomerization treatment method, wherein the hydroisomerization catalyst of the present invention is used. The hydroisomerization of the present invention can comprises the treatment step(s) well known in the art, as long as the catalyst of the present invention is used in the hydroisomerization. The hydroisomerization is one of the important reaction steps in the petroleum refining process, and mainly used in the production of high-quality fuel oil and high-grade lubricating oil. Among others, through the isomerization reactions of a normal paraffin having a higher freezing point and a long side-chain alkyl bonded to aromatic hydrocarbon in the feedstock oil, the light paraffin can produce a high-octane gasoline blending component, and for the long-chain alkane, the low-temperature flow properties of middle distillates (jet fuel and diesel) and lubricating oils may be improved.

In an embodiment of the present invention, the feedstock for the hydroisomerization is a hydrocracking tail oil. In an embodiment of the present invention, the hydrocracking tail oil is contacted with the hydroisomerization catalyst of the present invention under the hydroisomerization reaction conditions to undergo the hydroisomerization reaction. The distillation range of said hydrocracking tail oil is generally 350-500° C. (measured with a simulation distillation method under ordinary pressure).

In the present invention, the hydroisomerization reaction conditions are not particularly limited, as long as it is sufficient to cause the feedstock oil to undergo the hydroisomerization reaction. Generally, the hydroisomerization reaction conditions may include: the temperature is 200-500° C., preferably 250-400° C., more preferably 300-350° C.; the pressure is 1-30 MPa, preferably 2-20 MPa, more preferably 5-20 MPa. The pressure mentioned in the present invention refers to an absolute pressure. In the hydroisomerization process, the space velocity is 0.1-5 h$^{-1}$, preferably 0.1-3 h$^{-1}$, more preferably 0.5-2 h$^{-1}$; the hydrogen to oil volume ratio is 50-3000, preferably 300-3000, more preferably 400-600.

By the hydroisomerization process of the present invention, the hydrocracking tail oil is contacted with the hydroisomerization catalyst of the present invention to undergo the hydroisomerization reaction, which can achieve a higher yield of the isomerization product. Moreover, the resulting isomerization product has a higher viscosity index and a lower pour point, and is suitable as the base oil of the lubricating oil.

EXAMPLES

The present invention is described in detail below in conjunction with examples, but it does not limit the scope of the present invention.

In the following Examples and Comparative Examples, by using a 3271E type X-ray fluorescence spectrometer (XRF, the sample preparation method: a pressed disc method, the measurement condition: an end window rhodium target, the tube voltage: 50 kV, and the tube current: 50 mA), commercially available from Rigaku Industrial Corporation (Japan), the content of each element in the measured sample is analyzed and determined, and the molar ratio of each oxide in each sample (the molecular sieve precursor or the molecular sieve) is determined.

In the following Examples and Comparative Examples, the X-ray diffraction pattern (XRD) of the molecular sieve is determined by using a standard method with an X-ray powder end diffractometer (for example, Germany Bruker Company, D8 Advance powder diffractometer, light source: Cu Kα ray, Ni filter, tube voltage: 40 kV, tube current: 40 mA, value: 0.15418 nm, step: 0.02°, 2θ scan range: 5°-55°). Before testing the sample, the crystallization of the sample of the molecular sieve is observed with a scanning electron microscope (SEM) to confirm that only one crystal is contained in the sample, that is to say, the sample of the molecular sieve is in a pure phase; and then based on that, the XRD test is carried out, so that it is guaranteed that no interference peak of other crystals is present in the diffraction peaks of the XRD spectrum. The sample is calcined at 600° C. for 3 hours before test.

The determination of the $^{27}$Al NMR spectrum is carried out by using the methods well known in the art, for example, the measuring method and conditions used in Guoliang Zhao et al, Applied Catalysis A: General 299 (2006) 167-174. It is well known in the art that in the $^{27}$Al NMR spectrum, the peaks at the chemical shift δ of 10 to 40 ppm is attributed to the characteristic peaks of the penta-coordinated aluminum, the peaks at the chemical shift δ of −10 to 10 ppm is attributed to the characteristic peaks of the hexa-coordinated aluminum, and the peaks at the chemical shift δ of 50 to 70 ppm is attributed to the characteristic peaks of the tetra-coordinated aluminum. Therefore, the content of the penta-coordinated aluminium (%)=the integrated area of the peaks of the penta-coordinated aluminium/the total integrated area of the peaks of the aluminium×100%.

In the following Examples and Comparative Examples, the specific surface area and the external surface area of the sample are measured by using the DIGISORB 2500-type automatic adsorption instrument (Micromeritics company, U.S.A.). Before the measurement, the sample is calcined at 600° C. for 3 hours. The measurement method is carried out according to ASTM D4222-98 standard method.

The mesopore surface area is measured with the method well known in the art, for example, by using the measurement method and conditions disclosed in the publication Danny Verboekend et al, CrystEngComm 2011, 13, 3408-3416.

In the following Examples and Comparative Examples, the contents of water and the organic templating agent in the molecular sieve are measured by thermogravimetric analysis (for example, using SDT Q600 Synchronous Thermal Analyzer, TA Company, USA, the weight loss curve of the test sample is measured, starting from 25° C. and warming up to 800° C. at a heating velocity of 10° C./minute in an oxygen atmosphere).

In the following Examples and Comparative Examples, the dry basis content refers to the ratio by percent of the weight of the product obtained by calcining a certain amount of the material in an air atmosphere in a muffle furnace at 600° C. for 4 hours to the weight of the material before the calcination. That is to say, dry basis content=(the weight of the product obtained after the calcination/the weight of the material before the calcination)×100%.

In the following Examples and Comparative Examples, the carbon content of the semi-finished catalyst product is analyzed and determined by using the EMIA-320V carbon sulfur analyzer manufactured by HORIBA Corporation, Japan.

In the following Examples and Comparative Examples, the viscosity index is measured according to the method in GB/T 1995-1998, and the pour point is measured according to the method in GB/T 3535.

Example 1-1

(1) Preparation of Crystallized Mother Liquor 6.05 g of white carbon black, 0.51 g of analytically pure aluminum sec-butoxide, and 18.4 mL of an aqueous tetraethylammonium hydroxide solution (40 wt %) were taken for use. 15 g of deionized water, a solution of tetraethyl ammonium hydroxide and aluminium sec-butoxide in deionized water (37 g) were mixed. Then white carbon black was added. The resulting mixture was stirred for 1 hour, then moved into a reaction vessel, and crystallized at 140° C. for 120 hours.

(2) Preparation of Filter Cake

The crystallized mother liquor prepared in step (1) was filtered until there was no filtrate on the filter cake, and then the filtration suction was continued for 5 minutes to produce a filter cake F-1-1. This filter cake F-1-1 was an aqueous molecular sieve precursor having a dry basis content of 11.2 wt %. The filter cake had a silica/alumina molar ratio of 30.2 and a template/alumina molar ratio of 1:5.

(3) Preparation of Molecular Sieve Precursor

In the atmospheric environment, in a calcining furnace, the filter cake F-1-1 was heated from room temperature up to 450° C. at a heating rate of 25° C./minute and maintained at same temperature for 4 hours. The molecular sieve precursor C-1-1 was obtained and its $^{27}$Al NMR spectrum was shown in FIG. 1.

(4) Hydrothermal Treatment and Preparation of Molecular Sieve Product

The molecular sieve precursor C-1-1 was added to an HCl solution having a concentration of 1M and subjected to a closed hydrothermal treatment. Among others, the liquid-to-solid ratio was 50, the temperature of the hydrothermal treatment was 180° C., and the time of the hydrothermal treatment was 3 hours. After the completion of the hydrothermal treatment, the product was filtered, water-washed until the pH of the filtrate was 7, dried at 120° C. for 4 hours, and calcined at 550° C. for 4 hours to obtain a Beta molecular sieve product H-1. The Beta molecular sieve had a silica/alumina molar ratio of 159.2. The mesopore surface area, the specific surface area and the ratio of the mesopore surface area to the specific surface area were shown in Table 1.

Figure 2:
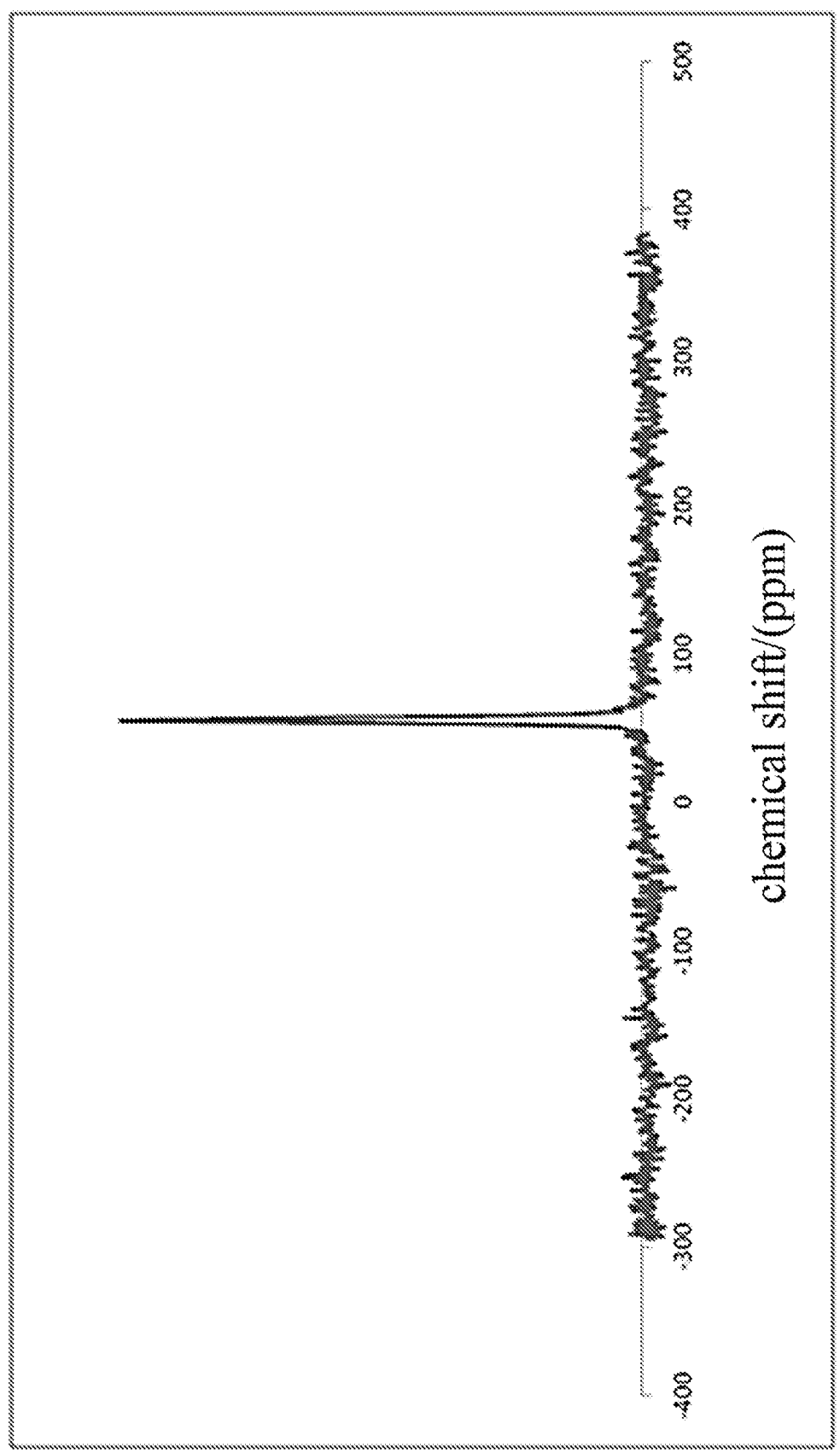
FIG. 2 is a $^{27}$Al NMR spectrum of the molecular sieve product H-1-1 prepared in Example 1-1.
Figure 3:
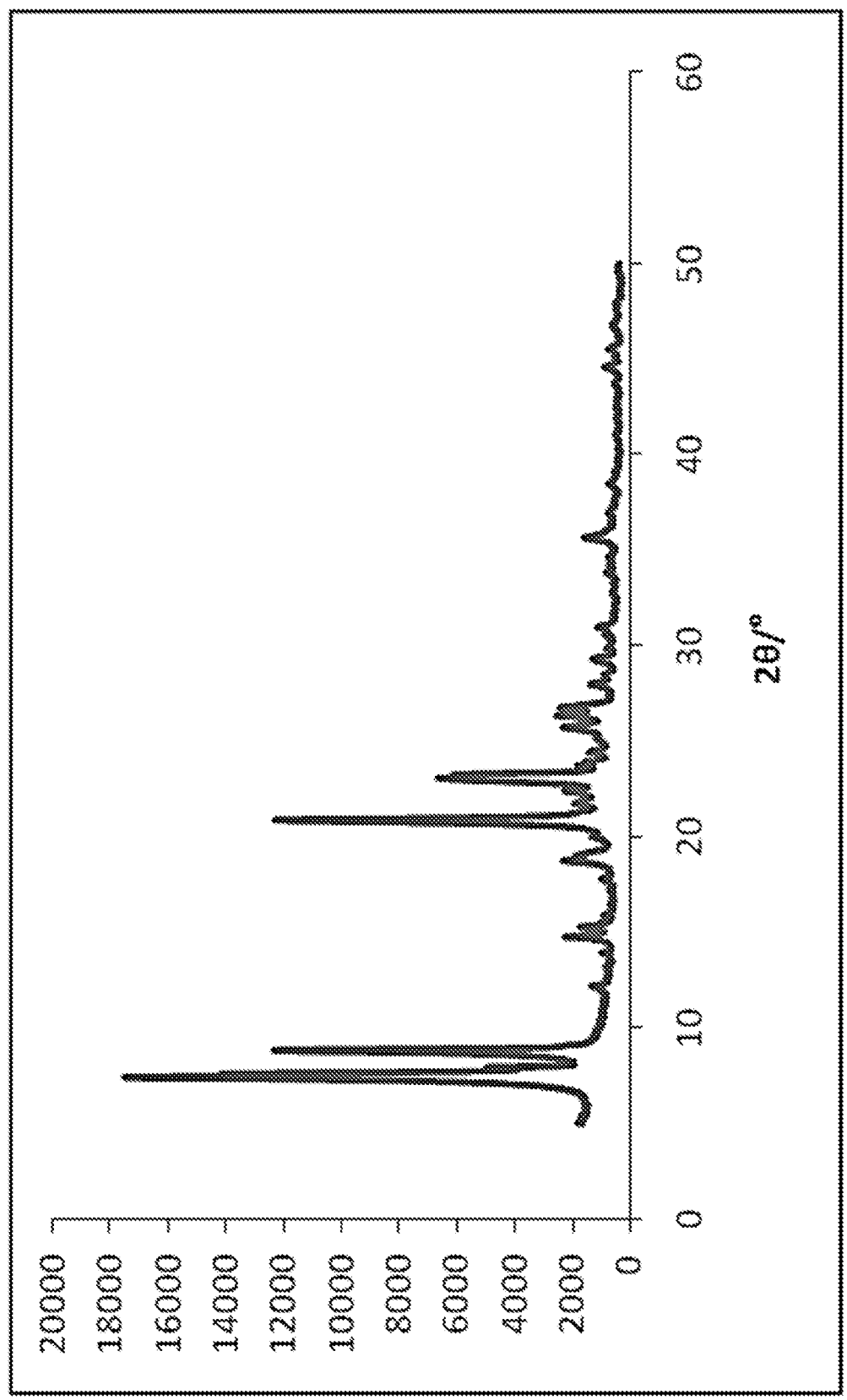
FIG. 3 is an XRD spectrum of the molecular sieve product H-1-1 prepared in Example 1-1.
Figure 4:
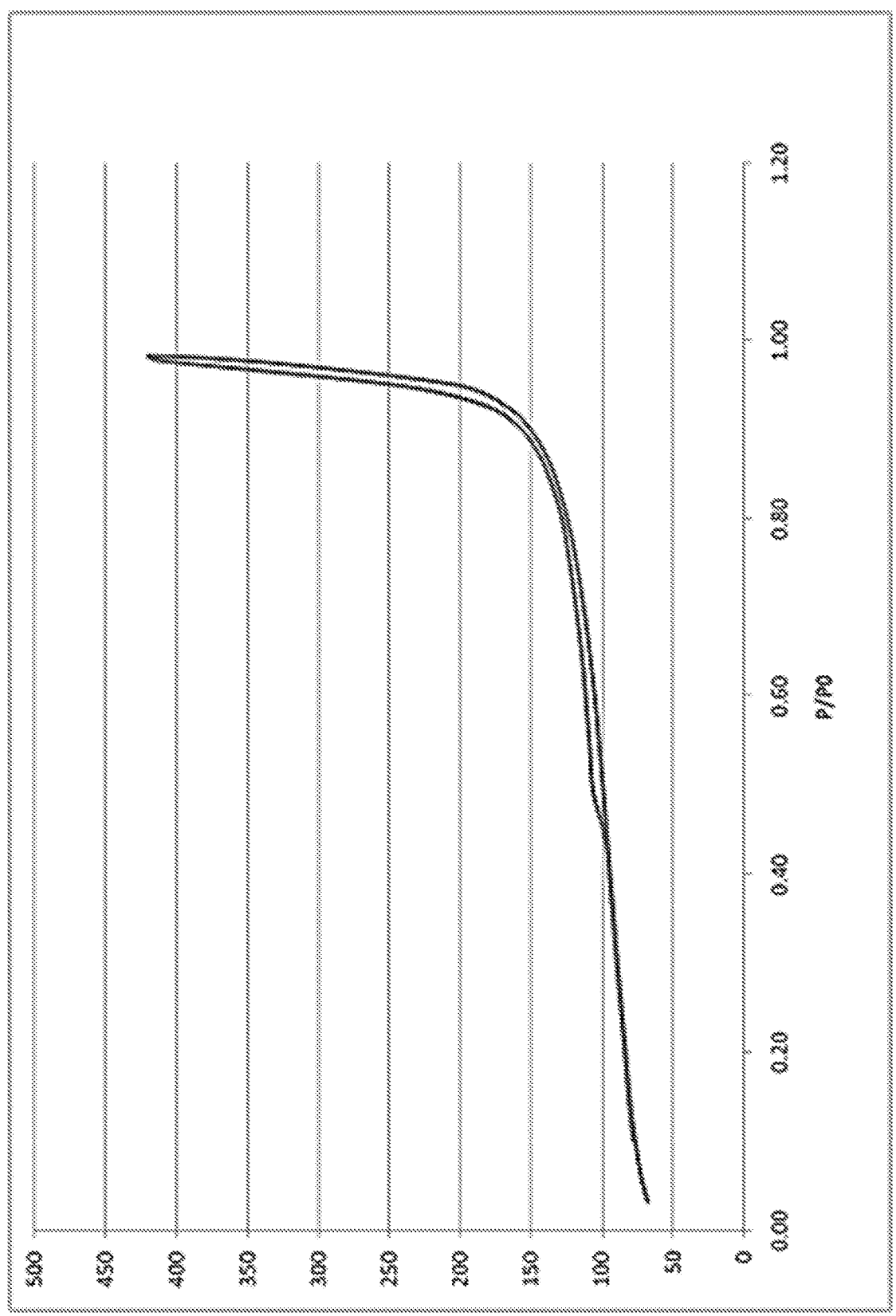
FIG. 4 is a nitrogen adsorption-desorption curve of the molecular sieve H-1-1 prepared in Example 1-1.

The XRD spectrum, the $^{27}$Al NMR spectrum and the nitrogen gas adsorption-desorption curve of the molecular sieve were respectively shown in FIG. 2, FIG. 3 and FIG. 4.

It can be seen from FIG. 4 that one closed hysteresis loop appeared in the range of $P/P_0$=0.4-0.99 in the low temperature nitrogen gas adsorption-desorption curve of the prepared molecular sieve, and the starting location of the closed hysteresis loop was in the range of $P/P_0$=0.4-0.5.

Comparative Example 1-1

A Beta molecular sieve was prepared according to the process of Example 1-1, except that in step (2), until there was no filtrate on the filter cake, the filtration suction was continued for 50 minutes to produce a filter cake DF-1-1. This filter cake DF-1-1 had a dry basis content of 46.5 wt %. Finally, a Beta molecular sieve product DH-1-1 was prepared. The Beta molecular sieve had a silica/alumina molar ratio of 122.7, and the mesopore surface area, the specific surface area and the ratio of the mesopore surface area to the specific surface area were shown in Table 1. One closed hysteresis loop appeared in the range of $P/P_0$=0.7-0.99 in the low temperature nitrogen gas adsorption-desorption curve of the prepared molecular sieve.

Example 1-2

A Beta molecular sieve was prepared according to the process of Example 1-1, except that in step (3), the filter cake F-1-1 was heated from room temperature up to 350° C. at a heating rate of 5° C./minute and maintained at same temperature for 14 hours. The calcining furnace was used in the heating process, and a molecular sieve precursor C-1-2 was obtained. A Beta molecular sieve product H-1-2 was prepared. The Beta molecular sieve had a silica/alumina molar ratio of 121.3, and the mesopore surface area, the specific surface area and the ratio of the mesopore surface area to the specific surface area were shown in Table 1. A closed hysteresis loop appeared in the range of $P/P_0$=0.4-0.99 in the low temperature nitrogen gas adsorption-desorption curve of the prepared molecular sieve, and the starting location of the closed hysteresis loop was in the range of $P/P_0$=0.4-0.5.

Example 1-3

A Beta molecular sieve was prepared according to the process of Example 1-1, except that in step (3), the filter cake F-1-1 was heated from room temperature up to 850° C. at a heating rate of 15° C./minute and maintained at same temperature for 4 hours. Air was introduced in the heating process, the air velocity was 1.0 liter/minute, and a molecular sieve precursor C-1-3 was obtained. A Beta molecular sieve product H-1-3 was prepared. The Beta molecular sieve had a silica/alumina molar ratio of 183.6, and the mesopore surface area, the specific surface area and the ratio of the mesopore surface area to the specific surface area were shown in Table 1. A closed hysteresis loop appeared in the range of $P/P_0$=0.4-0.99 in the low temperature nitrogen gas adsorption-desorption curve of the prepared molecular sieve, and the starting location of the closed hysteresis loop was in the range of $P/P_0$=0.4-0.5.

Example 1-4

A Beta molecular sieve was prepared according to the process of Example 1-1, except that in step (4), the molecular sieve precursor C-1-1 was added to a citric acid solution having a concentration of 1.0M and subjected to a closed hydrothermal treatment. Among others, the liquid-to-solid ratio was 100, the temperature of the hydrothermal treatment was 180° C., and the time of the hydrothermal treatment was 2 hours. After the completion of the hydrothermal treatment, the product was filtered, water-washed until the pH of the filtrate was 7, dried at 120° C. for 4 hours, and calcined at 550° C. for 4 hours to obtain a Beta molecular sieve product H-1-4. The Beta molecular sieve had a silica/alumina molar ratio of 168.2, and the mesopore surface area, the specific surface area and the ratio of the mesopore surface area to the specific surface area were shown in Table 1. A closed hysteresis loop appeared in the range of $P/P_0$=0.4-0.99 in the low temperature nitrogen gas adsorption-desorption curve of the prepared molecular sieve, and the starting location of the closed hysteresis loop was in the range of $P/P_0$=0.4-0.5.

Example 1-5

A Beta molecular sieve was prepared according to the process of Example 1-1, except that in step (4), the molecular sieve precursor C-1-1 was added to a citric acid solution having a concentration of 0.05M and subjected to a closed hydrothermal treatment. Among others, the liquid-to-solid ratio was 10, the temperature of the hydrothermal treatment was 90° C., and the time of the hydrothermal treatment was 0.1 hour. After the completion of the hydrothermal treatment, the product was filtered, water-washed until the pH of the filtrate was 7, dried at 120° C. for 4 hours, and calcined at 550° C. for 4 hours to obtain a Beta molecular sieve product H-1-5. The Beta molecular sieve had a silica/alumina molar ratio of 159.3, and the mesopore surface area, the specific surface area and the ratio of the mesopore surface area to the specific surface area were shown in Table 1. A closed hysteresis loop appeared in the range of $P/P_0$=0.4-0.99 in the low temperature nitrogen gas adsorption-desorption curve of the prepared molecular sieve, and the starting location of the closed hysteresis loop was in the range of $P/P_0$=0.4-0.5.

Example 1-6

A Beta molecular sieve was prepared according to the process of Example 1-1, except that in step (4), the molecular sieve precursor C-1-1 was added to a hydrochloric acid solution having a concentration of 1M and subjected to a closed hydrothermal treatment. Among others, the liquid-to-solid ratio was 50, the temperature of the hydrothermal treatment was 180° C., and the time of the hydrothermal treatment was 3 hours. After the completion of the hydrothermal treatment, the product was filtered, water-washed until the pH of the filtrate was 4, dried at 120° C. for 4 hours, and calcined at 550° C. for 4 hours to obtain a Beta molecular sieve product H-1-6. The Beta molecular sieve had a silica/alumina molar ratio of 158.5, and the mesopore surface area, the specific surface area and the ratio of the mesopore surface area to the specific surface area were shown in Table 1. A closed hysteresis loop appeared in the range of $P/P_0$=0.4-0.99 in the low temperature nitrogen gas adsorption-desorption curve of the prepared molecular sieve, and the starting location of the closed hysteresis loop was in the range of $P/P_0$=0.4-0.5.

Example 1-7

(1) Preparation of Crystallized Mother Liquor 6.05 g of white carbon black, 0.34 g of analytically pure aluminum sec-butoxide, and 18.4 mL of an aqueous tetraethylammonium hydroxide solution (40 wt %) were taken for use. 15 g of deionized water, a solution of tetraethyl ammonium hydroxide and aluminium sec-butoxide in deionized water (37 g) were mixed. Then white carbon black was added. The resulting mixture was stirred for 1 hour, then moved into a reaction vessel, and crystallized at 140° C. for 120 hours.

(2) Preparation of Filter Cake

The crystallized mother liquor prepared in step (1) was filtered until there was no filtrate on the filter cake, and then the filtration suction was continued for 5 minutes to produce a filter cake F-1-7. This filter cake F-1-7 was an aqueous molecular sieve precursor having a dry basis content of 11.2 wt %. The filter cake had a silica/alumina molar ratio of 45.8 and a template/alumina molar ratio of 1:6.

(3) Preparation of Molecular Sieve Precursor

In the atmospheric environment, in a calcining furnace, the filter cake F-1-7 was heated from room temperature up to 450° C. at a heating rate of 25° C./minute and maintained at same temperature for 4 hours. A molecular sieve precursor C-1-7 was obtained.

(4) Hydrothermal Treatment and Preparation of Molecular Sieve Product

The molecular sieve precursor C-1-7 was added to an HCl solution having a concentration of 1M and subjected to a closed hydrothermal treatment. Among others, the liquid-to-solid ratio was 50, the temperature of the hydrothermal treatment was 180° C., and the time of the hydrothermal treatment was 3 hours. After the completion of the hydrothermal treatment, the product was filtered, water-washed until the pH of the filtrate was 7, dried at 120° C. for 4 hours, and calcined at 550° C. for 4 hours to obtain a Beta molecular sieve product H-7. The Beta molecular sieve had a silica/alumina molar ratio of 164.5, and the mesopore surface area, the specific surface area and the ratio of the mesopore surface area to the specific surface area were shown in Table 1. A closed hysteresis loop appeared in the range of $P/P_0$=0.4-0.99 in the low temperature nitrogen gas adsorption-desorption curve of the prepared molecular sieve, and the starting location of the closed hysteresis loop was in the range of $P/P_0$=0.4-0.5.

Example 1-8

(1) Preparation of Crystallized Mother Liquor 6.05 g of white carbon black, 0.68 g of analytically pure aluminum sec-butoxide, and 18.4 mL of an aqueous tetraethylammonium hydroxide solution (40 wt %) were taken for use. 15 g of deionized water, a solution of tetraethyl ammonium hydroxide and aluminium sec-butoxide in deionized water (37 g) were mixed. Then white carbon black was added. The resulting mixture was stirred for 1 hour, then moved into a reaction vessel, and crystallized at 140° C. for 120 hours.

(2) Preparation of Filter Cake

The crystallized mother liquor prepared in step (1) was filtered until there was no filtrate on the filter cake, and then the filtration suction was continued for 5 minutes to produce a filter cake F-1-8. This filter cake F-1-8 was the aqueous molecular sieve precursor having a dry basis content of 11.2 wt %. The filter cake had a silica/alumina molar ratio of 22.6 and a template/alumina molar ratio of 1:4.

(3) Preparation of Molecular Sieve Precursor

In the atmospheric environment, in a calcining furnace, the filter cake F-1-8 was heated from room temperature up to 450° C. at a heating rate of 25° C./minute and maintained at same temperature for 4 hours. A molecular sieve precursor C-1-8 was obtained.

(4) Hydrothermal Treatment and Preparation of Molecular Sieve Product

The molecular sieve precursor C-1-8 was added to an HCl solution having a concentration of 1M and subjected to a closed hydrothermal treatment. Among others, the liquid-to-solid ratio was 50, the temperature of the hydrothermal treatment was 180° C., and the time of the hydrothermal treatment was 3 hours. After the completion of the hydrothermal treatment, the product was filtered, water-washed until the pH of the filtrate was 7, dried at 120° C. for 4 hours, and calcined at 550° C. for 4 hours to obtain a Beta molecular sieve product H-8. The Beta molecular sieve had a silica/alumina molar ratio of 145.6, the mesopore surface area, the specific surface area and the ratio of the mesopore surface area to the specific surface area were shown in Table 1. A closed hysteresis loop appeared in the range of $P/P_0=0.4$-$0.99$ in the low temperature nitrogen gas adsorption-desorption curve of the prepared molecular sieve, and the starting location of the closed hysteresis loop was in the range of $P/P_0=0.4$-$0.5$.

Comparative Example 1-2

Figure 5:
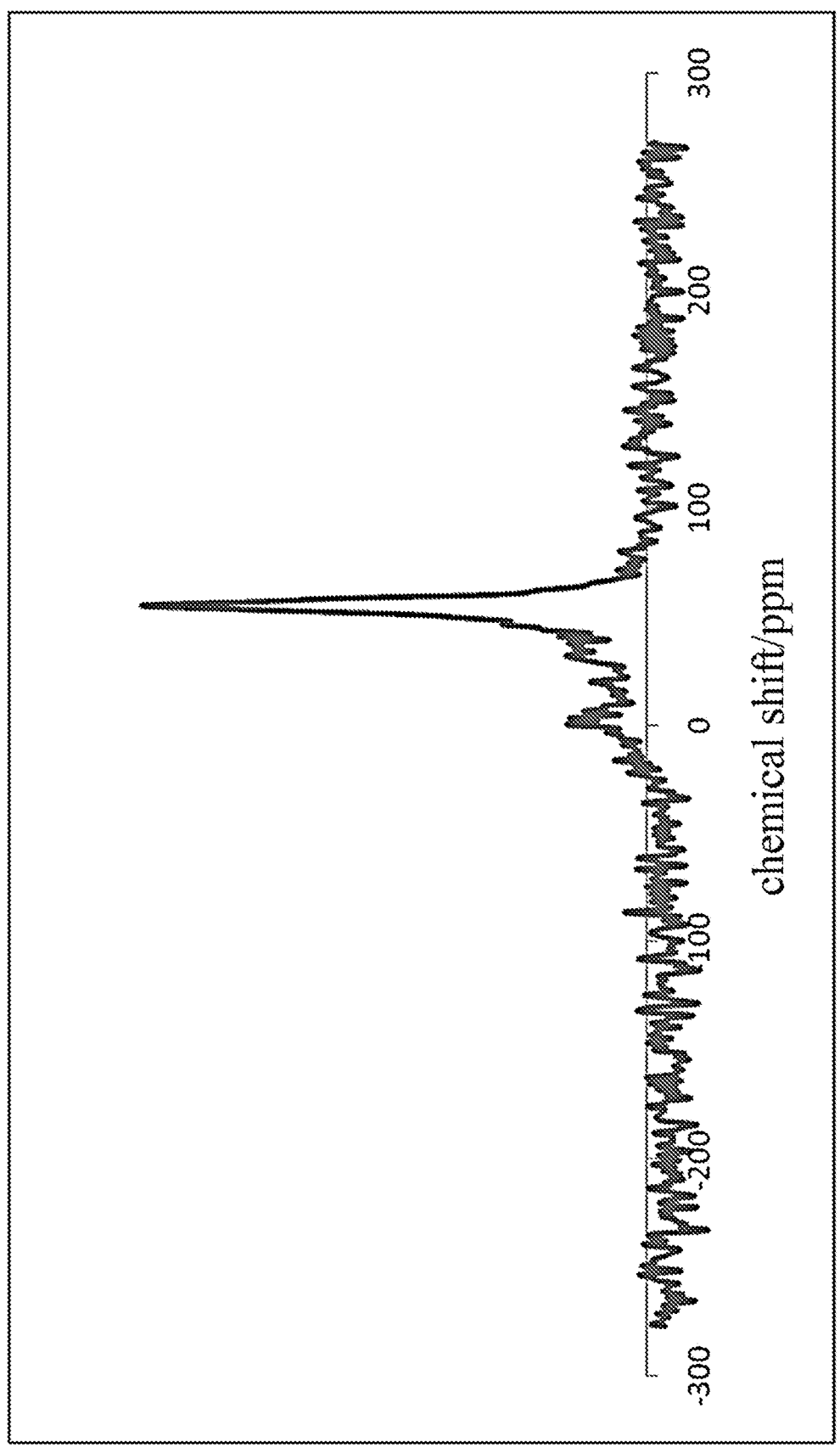
FIG. 5 is a $^{27}$Al NMR spectrum of the molecular sieve precursor DC-1-2 prepared in Comparative Example 1-2.
Figure 6:
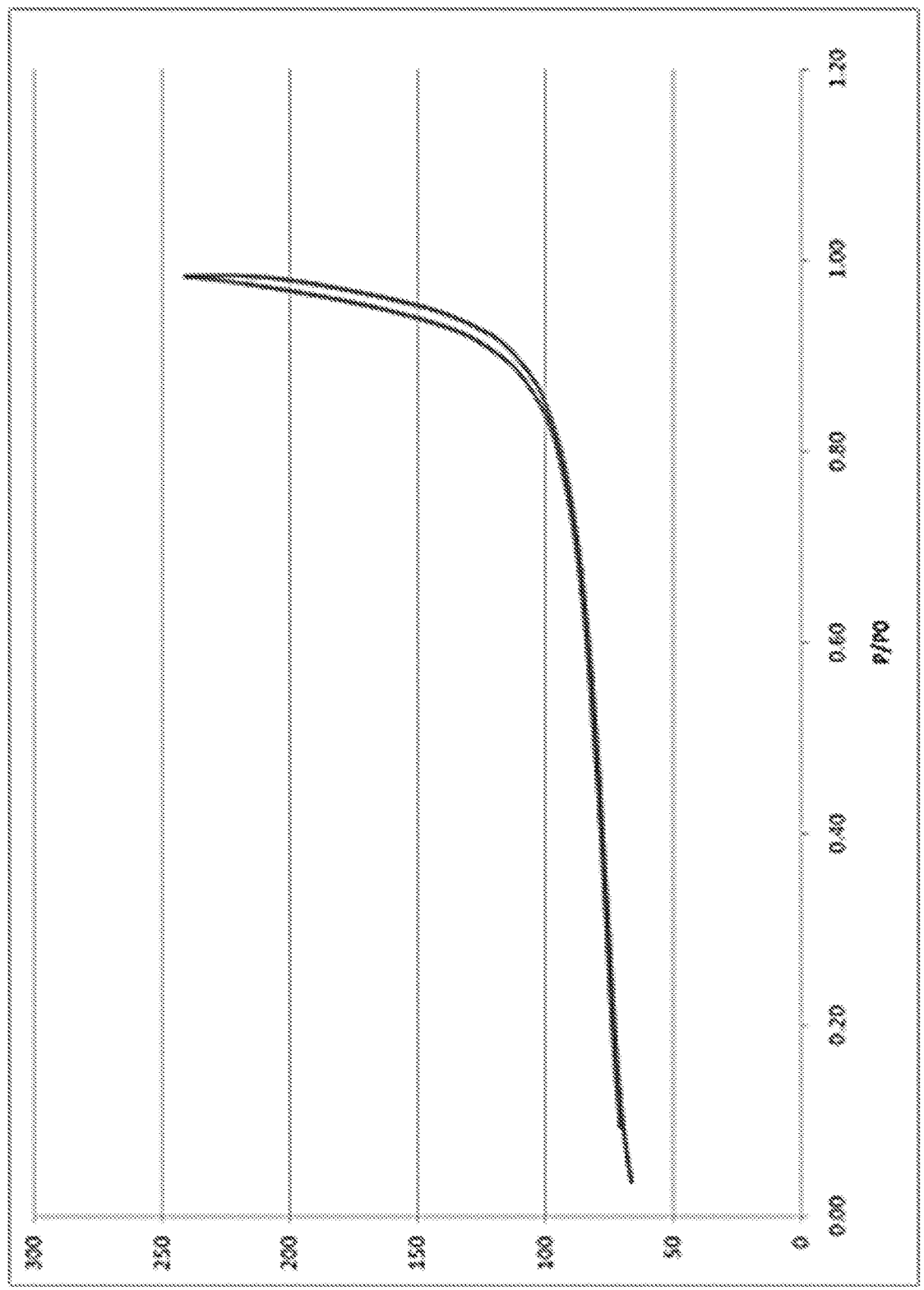
FIG. 6 is a nitrogen gas adsorption-desorption curve of the molecular sieve product DH-1-2 prepared in Comparative Example 1-2.

The crystallized mother liquor was prepared according to the step (1) of Example 1-1. Then the crystallized mother liquor was filtered. The filter cake obtained was dried at 120° C. for 4 hours, thus the filter cake was sufficiently dried, and then calcined at 550° C. for 4 hours to obtain a molecular sieve precursor DC-1-2. The molecular sieve precursor DC-1-2 and 10-fold volume of 0.5M hydrochloric acid solution were subjected to ammonium exchange treatment at 90° C. for 4 hours, and then filtered, dried and calcined at 550° C. for 4 hours to obtain a Beta molecular sieve product DH-1-2. The Beta molecular sieve had a silica/alumina molar ratio of 32.3, and the mesopore surface area, the specific surface area and the ratio of the mesopore surface area to the specific surface area were shown in Table 1. Its $^{27}$Al NMR spectrum was shown in FIG. 5, and its nitrogen gas adsorption-desorption curve was shown in FIG. 6. It could be seen from the figure that one closed hysteresis loop appeared in the range of $P/P_0=0.7$-$0.99$ in the low temperature nitrogen gas adsorption-desorption curve of the molecular sieve.

Test Example 1-1

(1) The mesopore surface area and the specific surface area of the molecular sieve products prepared in the Examples 1-1 to 1-8 and Comparative Examples 1-1 to 1-2 measured with the DIGISORB 2500-type automatic adsorption instrument (Micromeritics company, U.S.A.), and the proportion of the mesopore surface area in the specific surface area was calculated (mesopore surface area proportion=mesopore surface area/specific surface area× 100%). The result was shown in the below Table 1.

(2) The contents of each element in the molecular sieve precursors and the molecular sieve products prepared in the Examples 1-1 to 1-8 and Comparative Examples 1-1 to 1-2 were analyzed and determined by using a 3271E type X-ray fluorescence spectrometer commercially available from Rigaku Industrial Corporation (Japan), and the silica-alumina ratio was determined. The result was shown in the below Table 1.

TABLE 1

| | Molecular Sieve Precursor Content of Penta-Coordinated Aluminium (%) | Silica-Alumina Ratio | Content of Penta-Coordinated Aluminium (%) | Specific Surface Area | Mesopore Surface Area | Mesopore Surface Area Proportion |
|---|---|---|---|---|---|---|
| Example 1-1 | 28.2 | 159.2 | 0 | 241 m$^2$/g | 91 m$^2$/g | 37.8% |
| Comparative Example 1-1 | 2.4 | 122.7 | 0 | 240 m$^2$/g | 42 m$^2$/g | 17.5% |
| Example 1-2 | 2.3 | 121.3 | 0 | 239 m$^2$/g | 38 m$^2$/g | 15.7% |
| Example 1-3 | 49.8 | 183.6 | 4.3 | 243 m$^2$/g | 79 m$^2$/g | 32.5% |
| Example 1-4 | 28.2 | 168.2 | 0 | 234 m$^2$/g | 87 m$^2$/g | 37.2% |
| Example 1-5 | 28.2 | 159.3 | 1.2 | 234 m$^2$/g | 77 m$^2$/g | 33.0% |
| Example 1-6 | 28.2 | 158.5 | 0 | 233 m$^2$/g | 92 m$^2$/g | 39.5% |
| Example 1-7 | 25.6 | 164.5 | 0 | 213 m$^2$/g | 82 m$^2$/g | 38.5% |
| Example 1-8 | 30.6 | 145.6 | 0 | 238 m$^2$/g | 102 m$^2$/g | 42.8% |
| Comparative Example 1-2 | 0 | 32.3 | 0 | 220 m$^2$/g | 23 m$^2$/g | 10.5% |

Application Examples 1-1 to 1-9 and Application Comparative Examples 1-1 to 1-2

The molecular sieve products prepared in the Examples 1-1 to 1-8 and Comparative Examples 1-1 to 1-2 were mixed with 40 g of alumina, the resulting mixtures were extruded into strips, and the strips were dried to obtain the support strips E-1-1 to E-1-8 and DE-1-1 to DE-1-2, respectively.

1 g of tetraammineplatinum dichloride and 3.2 g of citric acid were added into 100 g of deionized water, and the mixture was stirred until uniform to prepare an impregnation solution. 80 g of the said support strips were respectively added into the said solution and impregnated for 4 hours at room temperature to produce catalyst precursors. Subsequently, the catalyst precursors were dried at 120° C. for 4 hours. Then they were calcined in a state of introducing an air flow, wherein the calcination temperature was 450° C., the time was 4 hours, and the air-to-catalyst ratio was 2.0 liters/(gram·hour) to produce semi-finished catalysts. The semi-finished catalysts were added to a solution of 3.2 g of citric acid in 100 g of deionized water, impregnated for 4 hours, dried at 120° C. for 4 hours, to obtain catalysts Cat-1-1 to Cat-1-8 and comparative catalysts D-Cat-1-1 to D-Cat-1-2, respectively.

In addition, 1 g of magnesium nitrate, 1 g of tetraammineplatinum dichloride, and 3.2 g of citric acid were added into 100 g of deionized water, and the mixture was stirred until uniform to get an impregnation solution. A catalyst Cat-1-9 was prepared by using the obtained impregnation solution and using E-1-1 as the support. This catalyst had a magnesium content as magnesium oxide of 0.33 wt %.

Test Example 1-2

100 g of 20-30 mesh of the catalysts Cat-1-1 to Cat-1-9 and D-Cat-1-1 to D-Cat-1-2 were put into a reaction tube respectively, and reduced under a hydrogen atmosphere for 4 hours, and the reduction temperature was 400° C., and the hydrogen pressure upon reduction was a normal atmospheric pressure. After the completion of the reduction, the temperature was lowered to 120° C. The hydrocracking tail oil was fed. The reaction temperature was 310° C. The tail oil volume space velocity was 1.0 $h^{-1}$. The hydrogen pressure was adjusted to 10.0 MPa, and the hydrogen flow rate was adjusted so that the hydrogen to oil volume ratio was 500. The feedstock amount was 195 g. The reaction time was 120 hours. The properties of the hydrocracking tail oil were shown below in Table 2. The evaluation results of catalysts were shown below in Table 3.

TABLE 2

| Analytic Item | Analytic Data | Analytic Method |
|---|---|---|
| Density at 20° C./(kg/m³) | 843.6 | SH/T0604-2000 |
| Kinematic Viscosity/(mm²/s) | | |
| 80° C. | 7.021 | GB/T 265-88 |
| 100° C. | 4.664 | GB/T 265-88 |
| Pouring Point/° C. | +42 | GB/T 3535 |
| Nitrogen Mass Fraction/(μg/g) | <1 | |
| Sulfur Mass Fraction/(μg/g) | 3 | SH/T 0842-2010 |

TABLE 3

| Catalyst | Pour Point | Yield/% | Viscosity Index |
|---|---|---|---|
| Cat-1-1 | −31 | 61.1 | 131 |
| Cat-1-2 | −25 | 55.3 | 130 |
| Cat-1-3 | −28 | 50.4 | 124 |
| Cat-1-4 | −32 | 61.2 | 133 |
| Cat-1-5 | −22 | 53.5 | 130 |
| Cat-1-6 | −23 | 60.3 | 132 |
| Cat-1-7 | −24 | 58.6 | 128 |
| Cat-1-8 | −26 | 60.3 | 130 |
| Cat-1-9 | −32 | 64.5 | 132 |
| D-Cat-1 | −17 | 39.2 | 114 |
| D-Cat-2 | −19 | 40.2 | 116 |

It could be seen from data in the above Table 3 that in case of using the Beta molecular sieve according to the present invention as the solid acid to form a catalyst and using the catalyst as a hydroisomerization catalyst, not only a better capacity of isomerization to reduce the freezing point was shown, but also the resulting product had a higher viscosity index, a high yield, and a low pour point.

Example 2-1

(1) Preparation of Crystallized Mother Liquor 36.3 g of silica sol containing 40 wt % of $SiO_2$, 1.77 g of analytically pure $Al_2(SO_4)_3 \cdot 18H_2O$, 3.94 g of analytically pure KOH and 8.44 g of hexamethylene diamine were taken for use. Hexamethylene diamine and silica sol were mixed. In addition, KOH and $Al_2(SO_4)_3 \cdot 18H_2O$ and 89.4 g of deionized water were mixed. Then two resulting solutions were mixed, stirred for 1 hour, then moved into a reaction vessel, and crystallized at 160° C. for 72 hours.

(2) Preparation of Filter Cake

The crystallized mother liquor prepared in step (1) was filtered until there was no filtrate on the filter cake, and then the filtration suction was continued for 5 minutes to produce a filter cake F-2-1. This filter cake F-2-1 was an aqueous molecular sieve precursor having a dry basis content of 11.2 wt %, a silica/alumina molar ratio of 30.2, a potassium oxide/alumina molar ratio of 2:1 and a template/alumina molar ratio of 1:8.

(3) Preparation of Molecular Sieve Precursor

Figure 7:
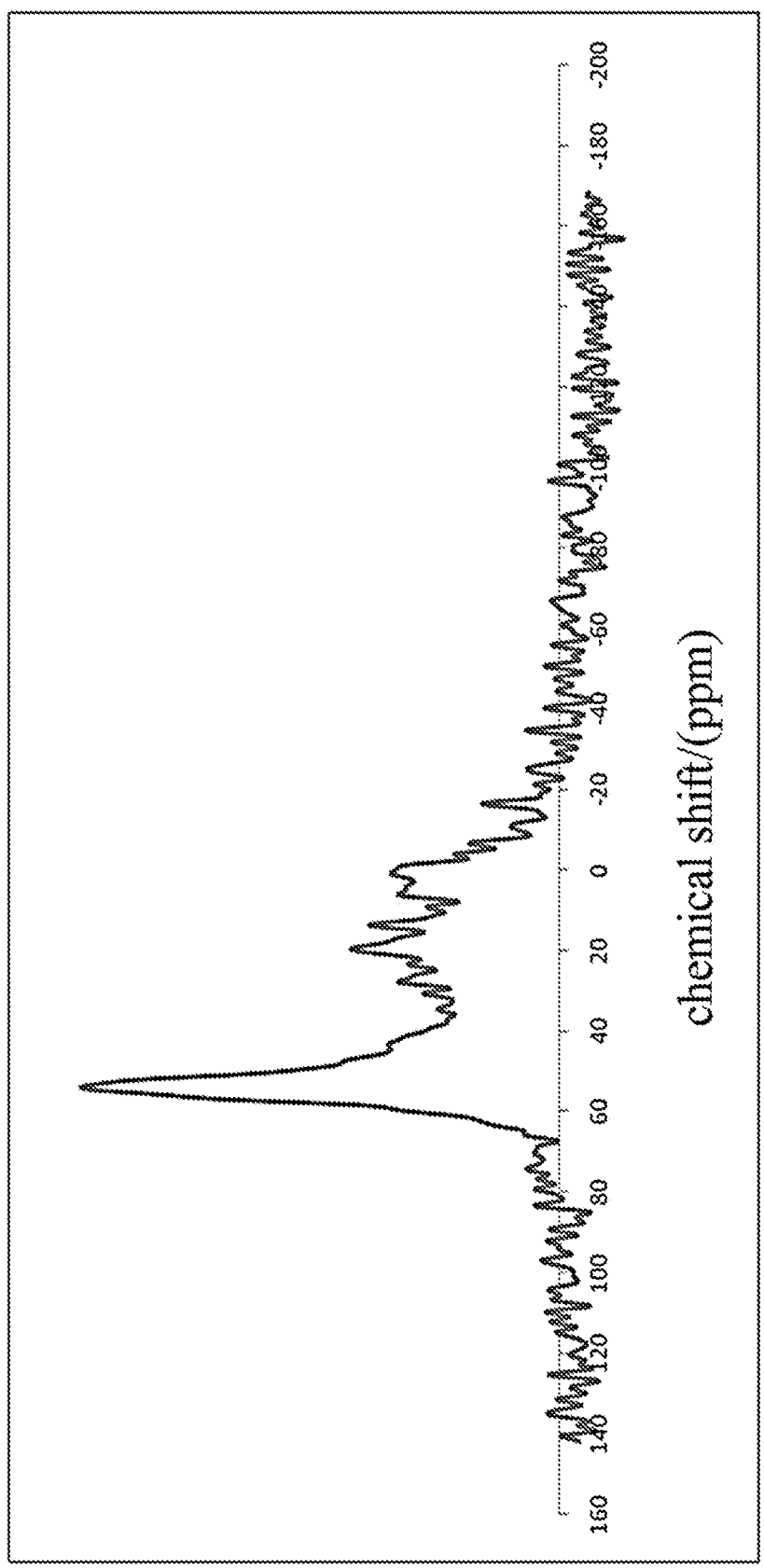
FIG. 7 is a $^{27}$Al NMR spectrum of the molecular sieve precursor C-2-1 prepared in Example 2-1.

In the atmospheric environment, in a calcining furnace, the filter cake F-2-1 was heated from room temperature up to 450° C. at a heating rate of 25° C./minute and maintained at same temperature for 4 hours. The molecular sieve precursor C-2-1 was obtained and its $^{27}Al$ NMR spectrum was shown in FIG. 7.

(4) Preparation of Molecular Sieve Product

The molecular sieve precursor C-2-1 was added to an HCl solution having a concentration of 1M and subjected to a closed hydrothermal treatment. Among others, the liquid-to-solid ratio was 50, the temperature of the hydrothermal treatment was 180° C., and the time of the hydrothermal treatment was 3 hours. After the completion of the hydrothermal treatment, the product was filtered, water-washed until the pH of the filtrate was 7, dried at 120° C. for 4 hours, and calcined at 550° C. for 4 hours to obtain a ZSM-22 molecular sieve product H-2-1. The ZSM-22 molecular sieve had a silica/alumina molar ratio of 165.2. The mesopore surface area, the specific surface area and the ratio of the mesopore surface area to the specific surface area was shown in Table 4.

Figure 8:
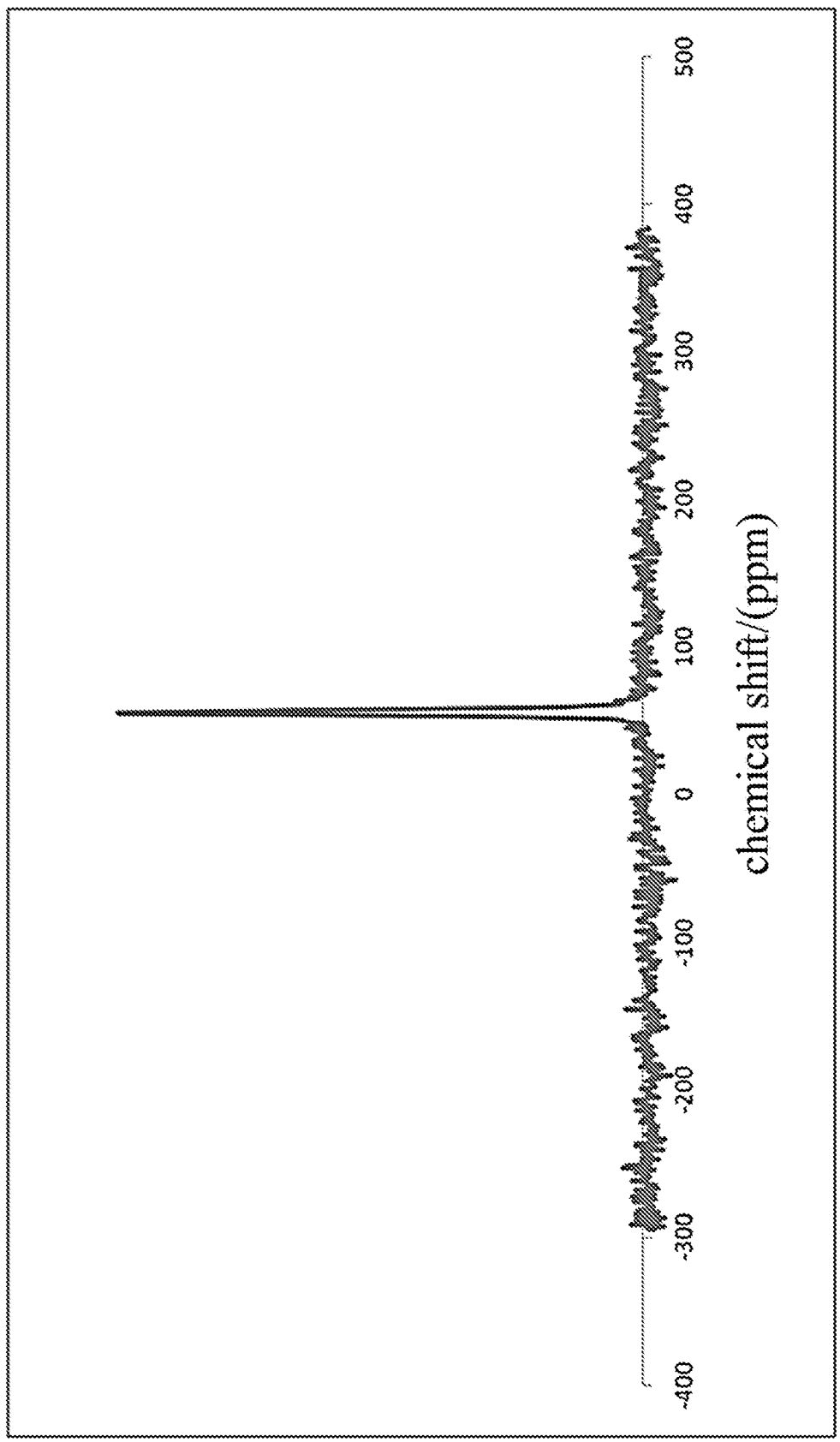
FIG. 8 is a $^{27}$Al NMR spectrum of the molecular sieve product H-2-1 prepared in Example 2-1.
Figure 9:
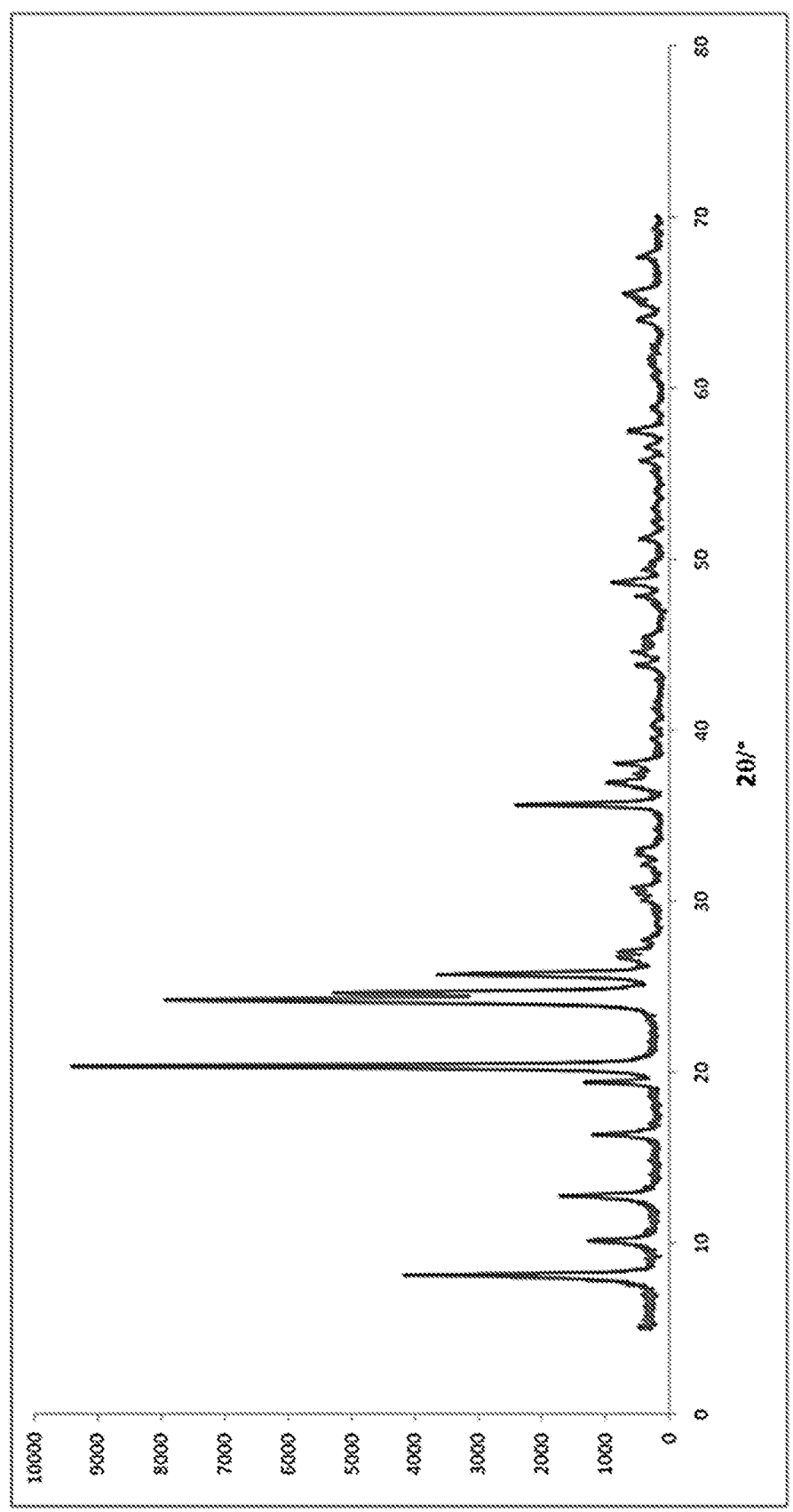
FIG. 9 is a XRD spectrum of the molecular sieve product H-2-1 prepared in Example 2-1.
Figure 10:
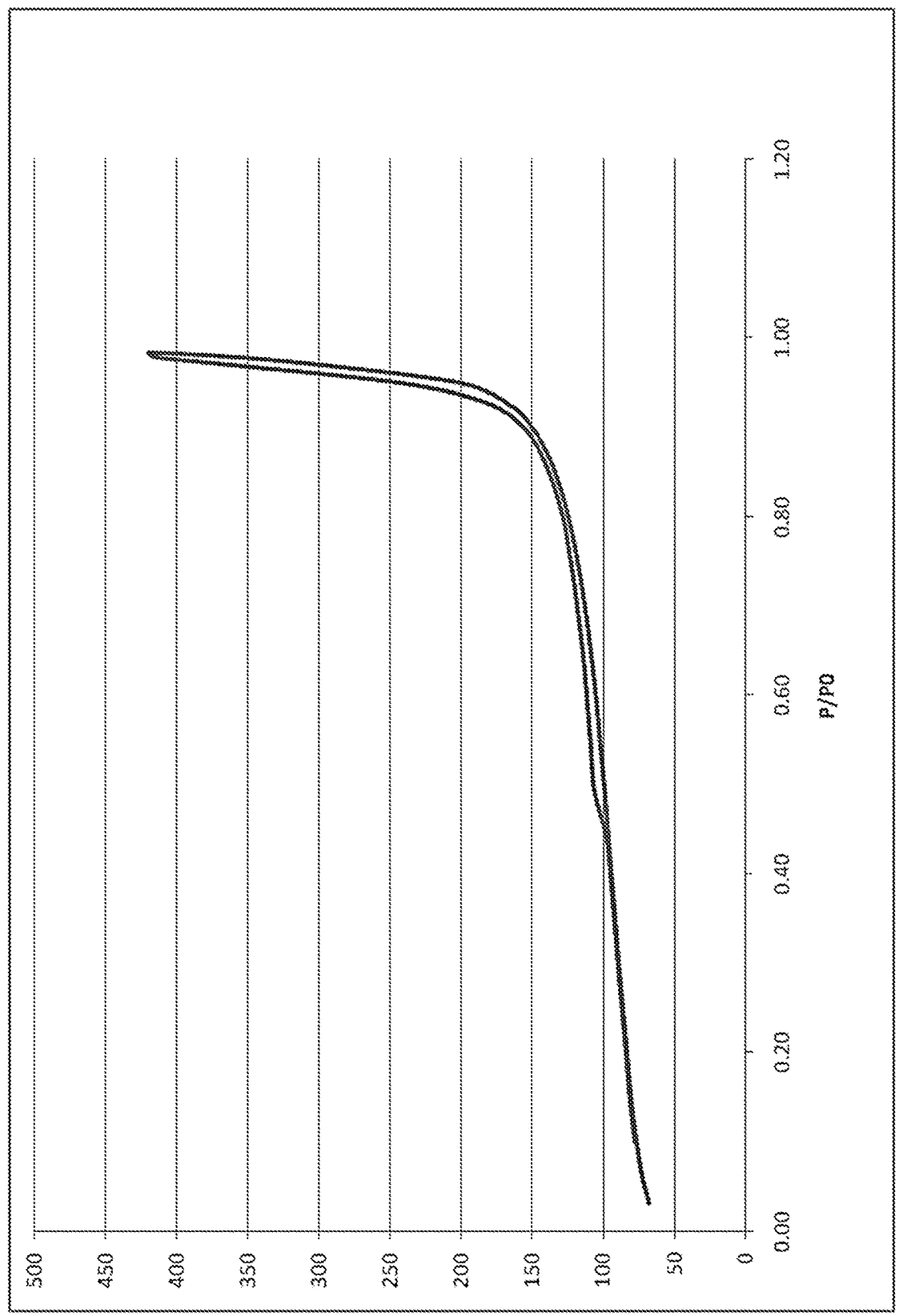
FIG. 10 is a nitrogen gas adsorption-desorption curve of the molecular sieve product H-2-1 prepared in Example 2-1.

The XRD spectrum, the $^{27}Al$ NMR spectrum and the nitrogen gas adsorption-desorption curve of the molecular sieve were respectively shown in FIG. 8, FIG. 9 and FIG. 10.

It can be seen from FIG. 10 that one closed hysteresis loop appeared in the range of $P/P_0=0.4$-0.99 in the low temperature nitrogen gas adsorption-desorption curve of the prepared ZSM-22 molecular sieve, and the starting location of the closed hysteresis loop was in the range of $P/P_0=0.4$-0.5.

Comparative Example 2-1

A ZSM-22 molecular sieve was prepared according to the process of Example 2-1, except that in step (2), until there was no filtrate on the filter cake, the filtration suction was continued for 50 minutes to produce a filter cake DF-2-1. This filter cake DF-2-1 had a dry basis content of 46.5 wt %. Finally, a ZSM-22 molecular sieve product DH-2-1 was prepared. The ZSM-22 molecular sieve had a silica/alumina molar ratio of 142.7, and the mesopore surface area, the specific surface area and the ratio of the mesopore surface area to the specific surface area were shown in Table 4. One closed hysteresis loop appeared in the range of $P/P_0=0.7$-

0.99 in the low temperature nitrogen gas adsorption-desorption curve of the prepared molecular sieve.

Example 2-2

A ZSM-22 molecular sieve was prepared according to the process of Example 2-1, except that in step (3), the filter cake F-2-1 was heated from room temperature up to 350° C. at a heating rate of 5° C./minute and maintained at same temperature for 14 hours. The calcining furnace was used in the heating process, and a molecular sieve precursor C-2-2 was obtained. Finally, a ZSM-22 molecular sieve product H-2-2 was prepared. The ZSM-22 molecular sieve had a silica/alumina molar ratio of 141.3, and the mesopore surface area, the specific surface area and the ratio of the mesopore surface area to the specific surface area were shown in Table 4. A closed hysteresis loop appeared in the range of $P/P_0=0.4$-0.99 in the low temperature nitrogen gas adsorption-desorption curve of the prepared molecular sieve, and the starting location of the closed hysteresis loop was in the range of $P/P_0=0.4$-0.5.

Example 2-3

A ZSM-22 molecular sieve was prepared according to the process of Example 2-1, except that in step (3), the filter cake F-2-1 was heated from room temperature up to 850° C. at a heating rate of 15° C./minute and maintained at same temperature for 4 hours. Air was introduced in the heating process, the air velocity was 1.0 liter/minute, and a molecular sieve precursor C-1-3 was obtained. Finally, a ZSM-22 molecular sieve product H-1-3 was prepared. The ZSM-22 molecular sieve had a silica/alumina molar ratio of 182.6, and the mesopore surface area, the specific surface area and the ratio of the mesopore surface area to the specific surface area were shown in Table 4. A closed hysteresis loop appeared in the range of $P/P_0=0.4$-0.99 in the low temperature nitrogen gas adsorption-desorption curve of the prepared molecular sieve, and the starting location of the closed hysteresis loop was in the range of $P/P_0=0.4$-0.5.

Example 2-4

A ZSM-22 molecular sieve was prepared according to the process of Example 2-1, except that in step (4), the molecular sieve precursor C-2-1 was added to a citric acid solution having a concentration of 1.0M and subjected to a closed hydrothermal treatment. Among others, the liquid-to-solid ratio was 100, the temperature of the hydrothermal treatment was 180° C., and the time of the hydrothermal treatment was 2 hours. After the completion of the hydrothermal treatment, the product was filtered, water-washed until the pH of the filtrate was 7, dried at 120° C. for 4 hours, and calcined at 550° C. for 4 hours to obtain a ZSM-22 molecular sieve product H-2-4. The ZSM-22 molecular sieve had a silica/alumina molar ratio of 172.2, and the mesopore surface area, the specific surface area and the ratio of the mesopore surface area to the specific surface area were shown in Table 4. A closed hysteresis loop appeared in the range of $P/P_0=0.4$-0.99 in the low temperature nitrogen gas adsorption-desorption curve of the prepared molecular sieve, and the starting location of the closed hysteresis loop was in the range of $P/P_0=0.4$-0.5.

Example 2-5

A ZSM-22 molecular sieve was prepared according to the process of Example 2-1, except that in step (4), the molecular sieve precursor C-2-1 was added to a citric acid solution having a concentration of 0.05M and subjected to a closed hydrothermal treatment. Among others, the liquid-to-solid ratio was 10, the temperature of the hydrothermal treatment was 90° C., and the time of the hydrothermal treatment was 0.1 hour. After the completion of the hydrothermal treatment, the product was filtered, water-washed until the pH of the filtrate was 7, dried at 120° C. for 4 hours, and calcined at 550° C. for 4 hours to obtain a ZSM-22 molecular sieve product H-2-5. The ZSM-22 molecular sieve had a silica/alumina molar ratio of 162.3, and the mesopore surface area, the specific surface area and the ratio of the mesopore surface area to the specific surface area were shown in Table 4. A closed hysteresis loop appeared in the range of $P/P_0=0.4$-0.99 in the low temperature nitrogen gas adsorption-desorption curve of the prepared molecular sieve, and the starting location of the closed hysteresis loop was in the range of $P/P_0=0.4$-0.5.

Example 2-6

A ZSM-22 molecular sieve was prepared according to the process of Example 2-1, except that in step (4), the molecular sieve precursor C-2-1 was added to a hydrochloric acid solution having a concentration of 1M and subjected to a closed hydrothermal treatment. Among others, the liquid-to-solid ratio was 50, the temperature of the hydrothermal treatment was 180° C., and the time of the hydrothermal treatment was 3 hours. After the completion of the hydrothermal treatment, the product was filtered, water-washed until the pH of the filtrate was 4, dried at 120° C. for 4 hours, and calcined at 550° C. for 4 hours to obtain a ZSM-22 molecular sieve product H-2-6. The ZSM-22 molecular sieve had a silica/alumina molar ratio of 161.5, and the mesopore surface area, the specific surface area and the ratio of the mesopore surface area to the specific surface area were shown in Table 4. A closed hysteresis loop appeared in the range of $P/P_0=0.4$-0.99 in the low temperature nitrogen gas adsorption-desorption curve of the prepared molecular sieve, and the starting location of the closed hysteresis loop was in the range of $P/P_0=0.4$-0.5.

Example 2-7

(1) Preparation of Crystallized Mother Liquor 36.3 g of silica sol containing 40 wt % of $SiO_2$, 1.18 g of analytically pure $Al_2(SO_4)_3 \cdot 18H_2O$, 3.94 g of analytically pure KOH and 8.44 g of hexamethylene diamine were taken for use. Hexamethylene diamine and silica sol were mixed. In addition, KOH and $Al_2(SO_4)_3 \cdot 18H_2O$ and 89.4 g of deionized water were mixed. Then two resulting solutions were mixed, stirred for 1 hour, then moved into a reaction vessel, and crystallized at 160° C. for 72 hours.

(2) Preparation of Filter Cake

The crystallized mother liquor prepared in step (1) was filtered until there was no filtrate on the filter cake, and then the filtration suction was continued for 5 minutes to produce a filter cake F-2-7. This filter cake F-2-7 was an aqueous molecular sieve precursor having a dry basis content of 11.2 wt %, a silica/alumina molar ratio of 45.6, a potassium oxide/alumina molar ratio of 2:1 and a template/alumina molar ratio of 1:10.

(3) Preparation of Molecular Sieve Precursor

In the atmospheric environment, in a calcining furnace, the filter cake F-2-7 was heated from room temperature up to 450° C. at a heating rate of 25° C./minute and maintained at same temperature for 4 hours. A molecular sieve precursor C-2-7 was obtained.

(4) Preparation of Molecular Sieve Product

The molecular sieve precursor C-2-7 was added to an HCl solution having a concentration of 1M and subjected to a closed hydrothermal treatment. Among others, the liquid-to-solid ratio was 40, the temperature of the hydrothermal treatment was 180° C., and the time of the hydrothermal treatment was 3 hours. After the completion of the hydrothermal treatment, the product was filtered, water-washed until the pH of the filtrate was 7, dried at 120° C. for 4 hours, and calcined at 550° C. for 4 hours to obtain a ZSM-22 molecular sieve product H-2-7. The ZSM-22 molecular sieve had a silica/alumina molar ratio of 174.8, and the mesopore surface area, the specific surface area and the ratio of the mesopore surface area to the specific surface area were shown in Table 4. A closed hysteresis loop appeared in the range of $P/P_0=0.4$-0.99 in the low temperature nitrogen gas adsorption-desorption curve of the prepared molecular sieve, and the starting location of the closed hysteresis loop was in the range of $P/P_0=0.4$-0.5.

Example 2-8

(1) Preparation of Crystallized Mother Liquor 36.3 g of silica sol containing 40 wt % of $SiO_2$, 2.36 g of analytically pure $Al_2(SO_4)_3 \cdot 18H_2O$, 3.94 g of analytically pure KOH and 8.44 g of hexamethylene diamine were taken for use. Hexamethylene diamine and silica sol were mixed. In addition, KOH and $Al_2(SO_4)_3 \cdot 18H_2O$ and 89.4 g of deionized water were mixed. Then two resulting solutions were mixed, stirred for 1 hour, then moved into a reaction vessel, and crystallized at 160° C. for 72 hours.

(2) Preparation of Filter Cake

The crystallized mother liquor prepared in step (1) was filtered until there was no filtrate on the filter cake, and then the filtration suction was continued for 5 minutes to produce a filter cake F-2-8. This filter cake F-2-8 was an aqueous molecular sieve precursor having a dry basis content of 11.2 wt %, a silica/alumina molar ratio of 22.8, a potassium oxide/alumina molar ratio of 2:1 and a template/alumina molar ratio of 1:7.

(3) Preparation of Molecular Sieve Precursor

In the atmospheric environment, in a calcining furnace, the filter cake F-2-8 was heated from room temperature up to 450° C. at a heating rate of 25° C./minute and maintained at same temperature for 4 hours. A molecular sieve precursor C-2-8 was obtained.

(4) Preparation of Molecular Sieve Product

The molecular sieve precursor C-2-8 was added to an HCl solution having a concentration of 1M and subjected to a closed hydrothermal treatment. Among others, the liquid-to-solid ratio was 40, the temperature of the hydrothermal treatment was 180° C., and the time of the hydrothermal treatment was 3 hours. After the completion of the hydrothermal treatment, the product was filtered, water-washed until the pH of the filtrate was 7, dried at 120° C. for 4 hours, and calcined at 550° C. for 4 hours to obtain a ZSM-22 molecular sieve product H-2-8. The ZSM-22 molecular sieve had a silica/alumina molar ratio of 159.3, and the mesopore surface area, the specific surface area and the ratio of the mesopore surface area to the specific surface area were shown in Table 4. A closed hysteresis loop appeared in the range of $P/P_0=0.4$-0.99 in the low temperature nitrogen gas adsorption-desorption curve of the prepared molecular sieve, and the starting location of the closed hysteresis loop was in the range of $P/P_0=0.4$-0.5.

Comparative Example 2-2

Figure 11:
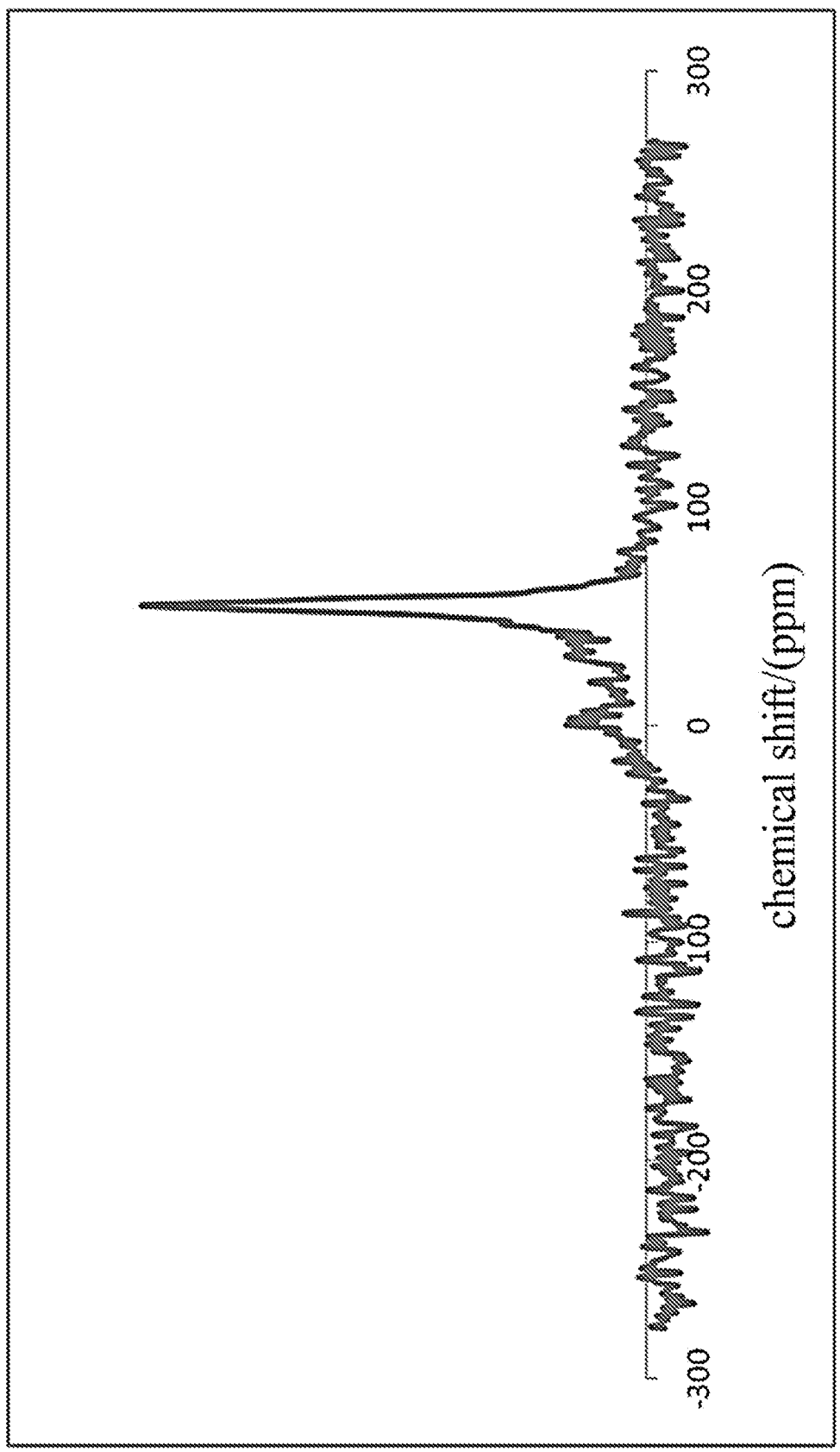
FIG. 11 is a $^{27}$Al NMR spectrum of the molecular sieve precursor DC-2-2 prepared in Comparative Example 2-2.
Figure 12:
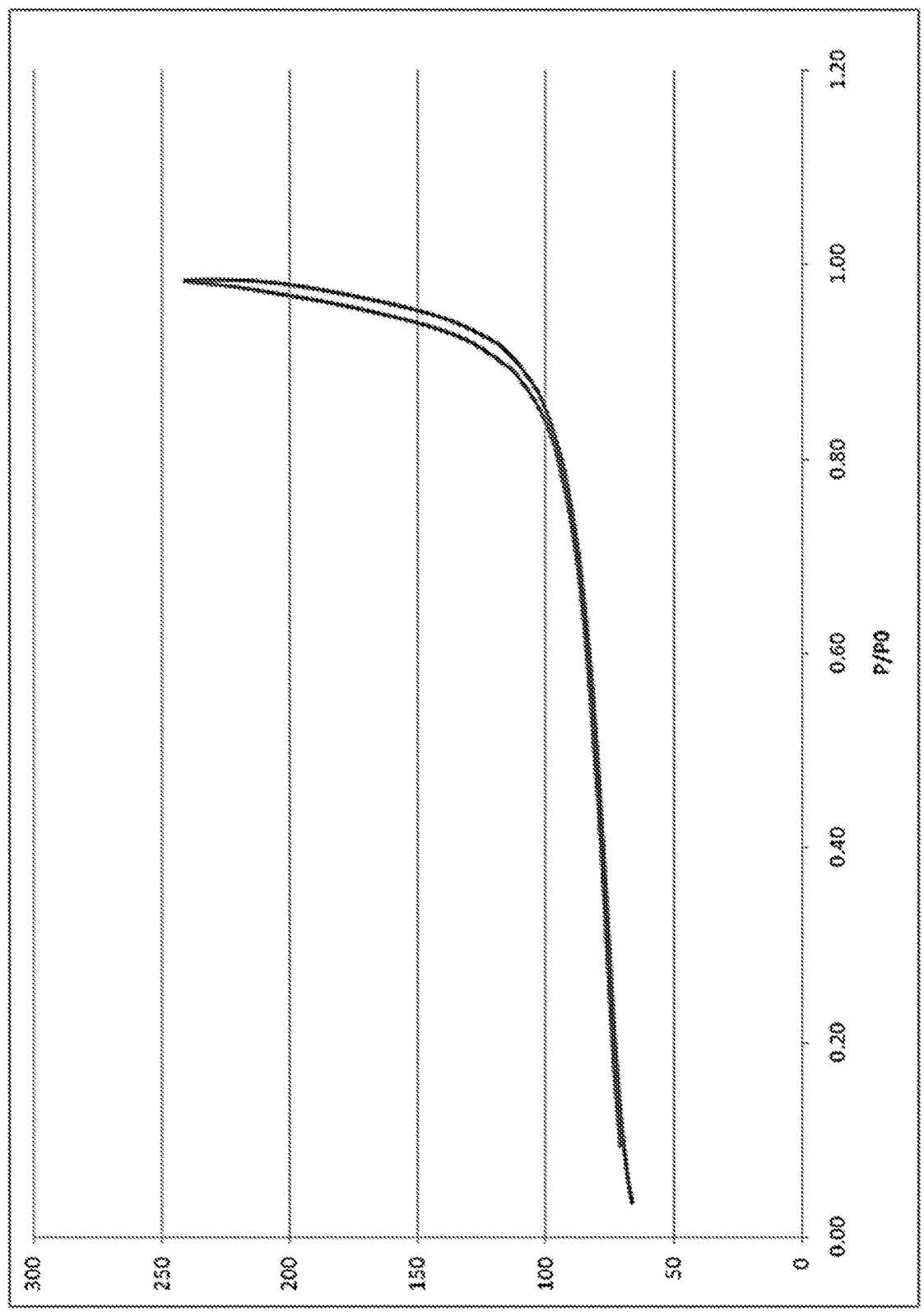
FIG. 12 is a nitrogen gas adsorption-desorption curve of the molecular sieve product DH-2-2 prepared in Comparative Example 2-2.

The crystallized mother liquor was prepared according to the step (1) of Example 2-1. Then the crystallized mother liquor was filtered. The filter cake obtained was dried at 120° C. for 4 hours. The filter cake was sufficiently dried, and then calcined at 550° C. for 4 hours to obtain a molecular sieve precursor DC-2-2. The molecular sieve precursor DC-2-2 and 10-fold volume of 0.5M hydrochloric acid solution were subjected to ammonium exchange treatment at 90° C. for 4 hours, and then filtered, dried and calcined at 550° C. for 4 hours to obtain a ZSM-22 molecular sieve product DH-2-2. The ZSM-22 molecular sieve had a silica/alumina molar ratio of 32.3, and the mesopore surface area, the specific surface area and the ratio of the mesopore surface area to the specific surface area were shown in Table 4. Its $^{27}Al$ NMR spectrum was shown in FIG. 11, and its nitrogen gas adsorption-desorption curve was shown in FIG. 12. It could be seen from the figure that one closed hysteresis loop appeared in the range of $P/P_0=0.7$-0.99 in the low temperature nitrogen gas adsorption-desorption curve of the molecular sieve.

Test Example 2-1

(1) The mesopore surface area and the specific surface area of the molecular sieve products prepared in the Examples 2-1 to 2-8 and Comparative Examples 2-1 to 2-2 measured with the DIGISORB 2500-type automatic adsorption instrument (Micromeritics company, U.S.A.), and the proportion of the mesopore surface area in the specific surface area was calculated. The result was shown in the below Table 4.

(2) The contents of each element in the molecular sieve precursors and the molecular sieve products prepared in the preparation Examples and preparation Comparative Examples were analyzed and determined by using a 3271E type X-ray fluorescence spectrometer commercially available from Rigaku Industrial Corporation (Japan), and the silica-alumina ratio was determined. The result was shown in the below Table 4.

TABLE 4

| | Molecular Sieve Precursor Content of | Molecular Sieve Product | | | | |
|---|---|---|---|---|---|---|
| | Penta-Coordinated Aluminium (%) | Silica-Alumina Ratio | Content of Penta-Coordinated Aluminium (%) | Specific Surface Area | Mesopore surface area | Mesopore surface area Proportion |
| Example 2-1 | 26.2 | 165.2 | 0 | 235 m²/g | 89 m²/g | 37.9% |
| Comparative Example 2-1 | 2.8 | 142.7 | 0 | 232 m²/g | 40 m²/g | 17.2% |
| Example 2-2 | 2.6 | 141.3 | 0 | 231 m²/g | 38 m²/g | 16.5% |
| Example 2-3 | 45.8 | 182.6 | 4.3 | 234 m²/g | 77 m²/g | 32.9% |
| Example 2-4 | 26.2 | 172.2 | 0 | 223 m²/g | 88 m²/g | 39.5% |
| Example 2-5 | 26.2 | 162.3 | 1.2 | 223 m²/g | 77 m²/g | 34.5% |
| Example 2-6 | 26.2 | 161.5 | 0 | 221 m²/g | 92 m²/g | 41.6% |
| Example 2-7 | 23.2 | 174.8 | 0 | 219 m²/g | 89 m²/g | 40.6% |
| Example 2-8 | 33.1 | 159.3 | 0 | 231 m²/g | 98 m²/g | 42.4% |
| Comparative Example 2-2 | 0 | 32.3 | 0 | 214 m²/g | 22 m²/g | 10.3% |

Application Example 2-1

40 g of the molecular sieve H-2-1 prepared in Example 2-1 was mixed with 40 g of alumina, the resulting mixture was extruded into strips, and the strips were dried to obtain the support E-2-1.

0.4 g of tetraammineplatinum dichloride, 0.6 g of tetraamminepalladium dichloride and 3.2 g of citric acid were added into 100 g of deionized water, and the mixture was stirred until uniform. 80 g of the support E-2-1 was added into said solution and impregnated for 4 hours at room temperature to produce a catalyst precursor. Subsequently, the catalyst precursor was dried at 120° C. for 4 hours. Then it was calcined in a state of introducing an air flow, wherein the calcination temperature was 450° C., the time was 4 hours, and the air-to-catalyst ratio was 2.0 liters/(gram·hour) to produce a semi-finished catalyst. The semi-finished catalyst was added to a solution of 3.2 g of citric acid in 100 g of deionized water, impregnated for 4 hours, dried at 120° C. for 4 hours to obtain a catalyst IC-1.

Application Examples 2-2 to 2-8 and Application Comparative Examples 2-1 to 2-2

The catalysts were prepared according to the process of Application Example 2-1, except for replacing the molecular sieve H-1-1 used in Application Example 2-1 with the molecular sieves H-2-2 to H-2-8 prepared in Examples 2-2 to 2-8 and the molecular sieves DH-2-1 to DH-2-2 prepared in Comparative Examples 2-1 to 2-2 respectively, to prepare catalysts IC-2 to IC-8 and comparative catalysts DIC-1 to DIC-2.

Application Example 2-9

The support E-2-1 was prepared according to the process of Application Example 2-1.

0.4 g of tetraammineplatinum dichloride, 0.6 g of tetraamminepalladium dichloride and 16 g of citric acid were added into 100 g of deionized water, and the mixture was stirred until uniform. 80 g of the support E-2-1 was added into said solution and impregnated for 4 hours at room temperature to produce a catalyst precursor. Subsequently, the catalyst precursor was dried at 120° C. for 4 hours. Then it was calcined in a state of introducing an air flow, wherein the calcination temperature was 450° C., the time was 4 hours, and the air-to-catalyst ratio was 2.0 liters/(gram·hour) to produce a semi-finished catalyst. The semi-finished catalyst was added to a solution of 16 g of citric acid in 100 g of deionized water, impregnated for 4 hours, dried at 120° C. for 4 hours to obtain a catalyst IC-9.

Application Example 2-10

The support E-2-1 was prepared according to the process of Application Example 2-1.

0.4 g of tetraammineplatinum dichloride, 0.6 g of tetraamminepalladium dichloride and 18 g of EDTA were added into 100 g of deionized water, and the mixture was stirred until uniform. 80 g of the support E-2-1 was added into said solution and impregnated for 4 hours at room temperature to produce a catalyst precursor. Subsequently, the catalyst precursor was dried at 120° C. for 4 hours. Then it was calcined in a state of introducing an air flow, wherein the calcination temperature was 450° C., the time was 4 hours, and the air-to-catalyst ratio was 2.0 liters/(gram·hour) to produce a semi-finished catalyst. The semi-finished catalyst was added to a solution of 6.4 g of diethylene glycol in 100 g of deionized water, impregnated for 4 hours, dried at 120° C. for 4 hours to obtain a catalyst IC-10.

Application Example 2-11

The support E-2-1 was prepared according to the process of Application Example 2-1.

0.4 g of tetraammineplatinum dichloride, 0.6 g of tetraamminepalladium dichloride and 20 g of butylene glycol were added into 100 g of deionized water, and the mixture was stirred until uniform. 80 g of the support E-2-1 was added into said solution and impregnated for 4 hours at room temperature to produce a catalyst precursor. Subsequently, the catalyst precursor was dried at 120° C. for 4 hours. Then it was calcined in a state of introducing an air flow, wherein the calcination temperature was 350° C., the time was 4 hours, and the air-to-catalyst ratio was 1.0 liters/(gram·hour) to produce a semi-finished catalyst. The semi-finished catalyst was added to a solution of 3.2 g of citric acid in 100 g of deionized water, impregnated for 4 hours, dried at 120° C. for 4 hours to obtain a catalyst IC-11.

Application Example 2-12

The support E-2-1 was prepared according to the process of Application Example 2-1.

0.4 g of tetraammineplatinum dichloride, 0.6 g of tetraamminepalladium dichloride and 19 g of ethylene diamine were added into 100 g of deionized water, and the mixture was stirred until uniform. 80 g of the support E-2-1 was added into said solution and impregnated for 4 hours at room temperature to produce a catalyst precursor. Subsequently, the catalyst precursor was dried at 120° C. for 4 hours. Then it was calcined in a state of introducing an air flow, wherein the calcination temperature was 350° C., the time was 4 hours, and the air-to-catalyst ratio was 1.0 liters/(gram·hour) to produce a semi-finished catalyst. The semi-finished catalyst was added to a solution of 1.0 g of citric acid in 100 g of deionized water, impregnated for 4 hours, dried at 120° C. for 4 hours to obtain a catalyst IC-12.

Application Example 2-13

The support E-2-1 was prepared according to the process of Application Example 2-1.

1 g of zinc nitrate, 0.4 g of tetraammineplatinum dichloride, 0.6 g of tetraamminepalladium dichloride and 19 g of ethylene diamine were added into 100 g of deionized water, and the mixture was stirred until uniform. 80 g of the support E-2-1 was added into said solution and impregnated for 4 hours at room temperature to produce a catalyst precursor. Subsequently, the catalyst precursor was dried at 120° C. for 4 hours to produce a catalyst precursor. Then it was calcined in a state of introducing an air flow, wherein the calcination temperature was 350° C., the time was 4 hours, and the air-to-catalyst ratio was 1.0 liters/(gram·hour) to produce a semi-finished catalyst. The semi-finished catalyst was added to a solution of 1.0 g of citric acid in 100 g of deionized water, impregnated for 4 hours, dried at 120° C. for 4 hours to obtain a catalyst IC-13. This catalyst had a zinc content as zinc oxide of 0.42 wt %.

Test Example 2-2

(1) In Application Examples and Application Comparative Examples, the carbon content of the semi-finished catalyst product was analyzed and measured by using the EMIA-320V carbon sulfur analyzer produced by HORIBA Corporation, Japan. The results were shown below in Table 6.

(2) 100 g of 20-30 mesh of the catalysts prepared in Application Examples and Application Comparative Examples were put into a reaction tube respectively, and reduced under a hydrogen atmosphere for 4 hours, wherein the reduction temperature was 400° C., and the hydrogen pressure upon reduction was a normal atmospheric pressure. After the completion of the reduction, the temperature was lowered to 120° C. The hydrocracking tail oil was fed. The reaction temperature was 310° C. The tail oil volume space velocity was 1.0 $h^{-1}$. The hydrogen pressure was adjusted to 10.0 MPa, and the hydrogen flow rate was adjusted so that the hydrogen to oil volume ratio was 500. The feedstock amount was 195 g. The reaction time was 120 hours. The properties of the hydrocracking tail oil were shown below in Table 5. The evaluation results of catalysts were shown below in Table 6.

TABLE 5

| Analytic Item | Analytic Data | Analytic Method |
|---|---|---|
| Density at 20° C./(kg/m$^3$) | 843.6 | SH/T0604-2000 |
| Kinematic Viscosity/(mm$^2$/s) | | |
| 80° C. | 7.021 | GB/T 265-88 |
| 100° C. | 4.664 | GB/T 265-88 |
| Pouring Point/° C. | +42 | GB/T 3535 |
| Nitrogen Mass Fraction/(μg/g) | <1 | |
| Sulfur Mass Fraction/(μg/g) | 3 | SH/T 0842-2010 |

TABLE 6

| | Carbon Content of Semi-Finished Catalyst/wt % | Catalyst Evaluation Result | | |
|---|---|---|---|---|
| | | Pour Point | Yield/% | Viscosity Index |
| Application Example 2-1 | 0.11 | −22 | 69.3 | 123 |
| Application Example 2-2 | 0.15 | −19 | 65.3 | 118 |
| Application Example 2-3 | 0.17 | −18 | 64.7 | 119 |
| Application Example 2-4 | 0.11 | −22 | 70.5 | 124 |
| Application Example 2-5 | 0.13 | −19 | 64.5 | 119 |
| Application Example 2-6 | 0.15 | −19 | 64.6 | 118 |
| Application Example 2-7 | 0.15 | −20 | 65.3 | 120 |
| Application Example 2-8 | 0.15 | −21 | 64.8 | 118 |
| Application Example 2-9 | 0.33 | −22 | 75.5 | 132 |
| Application Example 2-10 | 0.35 | −21 | 75.6 | 133 |
| Application Example 2-11 | 0.32 | −22 | 75.3 | 131 |
| Application Example 2-12 | 0.32 | −22 | 75.5 | 133 |
| Application Example 2-13 | 0.32 | −24 | 78.9 | 136 |
| Application Comparative Example 1 | 0.02 | −12 | 53.9 | 110 |
| Application Comparative Example 2 | 0.01 | −13 | 54.3 | 111 |

It could be seen from data in the above Table 6 that in case of using the hydroisomerization catalyst according to the present invention to hydrotreat the hydrocracking tail oil, the resulting product had a higher viscosity index, a lower pour point, and a higher yield.

INDUSTRIAL APPLICABILITY

The molecular sieve of the present invention has a high mesopore surface area, and the activity is greatly increased in case that the molecular sieve is used as the solid acid catalyst. Moreover, in case that the molecular sieve of the present invention is used as the support to prepare a catalyst, the catalytic activity of the resulting catalyst can also be increased and the physical properties of the resulting products are improved. Furthermore, the process for preparing the catalyst of the present invention can prepare a catalyst having a high dispersity of the active component on the support, thus not only the life period of the catalyst is prolonged, but also the catalytic activity of the catalyst is further increased.

The invention claimed is:

1. A molecular sieve having mesopores, comprising $Al_2O_3$ and $SiO_2$ at a molar ratio between $Al_2O_3$ and $SiO_2$ of 1:(150-200), wherein said molecular sieve has a framework of ZSM-22 or Beta molecular sieve, a low temperature nitrogen gas adsorption-desorption curve of said molecular sieve has one closed hysteresis loop appears in the range of $P/P_0$=0.4-0.99 between an adsorption branch and a desorption branch, and a starting location is in the range of $P/P_0$=0.4-0.6, and said molecular sieve has a mesopore surface area of 30 $m^2$/g-280 $m^2$/g.

2. The molecular sieve according to claim 1, wherein said molecular sieve has a mesopore surface area of 50 $m^2$/g-250 $m^2$/g.

3. The molecular sieve according to claim 1, wherein said molecular sieve has a specific surface area of 200 $m^2$/g-320 $m^2$/g.

4. The molecular sieve according to claim 1, wherein a ratio of the mesopore surface area to the molecular sieve surface area is 20%-70%.

5. The molecular sieve according to claim 1, wherein the starting location of the closed hysteresis loop is in the range of $P/P_0$=0.4-0.55.

6. The molecular sieve according to claim 1, wherein said molecular sieve has a penta-coordinated aluminium content ranging from 0% to 5%.

7. A process for preparing a molecular sieve of claim 1, comprising:

preparing a mother liquor, that is a mixture containing an alumina source, a silica source, a template agent, and water;

crystalizing the mother liquor under a crystallization condition to produce a crystallized mother liquor;

filtering the crystallized mother liquor to produce a wet filter cake having a dry basis content of 5 wt %-30 wt %;

calcining the wet filter cake to produce a molecular sieve precursor, wherein the calcination is carried out at 400-600° C. at a heating rate upon calcination of 5° C./minute–100° C./minute for 1 hour-20 hours;

subjecting said molecular sieve precursor to hydrothermal treatment in an acidic aqueous solution having an inorganic acid and/or organic acid content of 0.01M-5M at a liquid-solid volume ratio of 5-200 at 80° C.–300° C. for 0.1 hour-24 hours; and filtering the hydrothermally treated product, optionally washing and drying, and further calcining at 400° C.–600° C. for 2-8 hours.

8. The preparation process according to claim 7, wherein a molar ratio of the silica source to the alumina source in the mother liquor, based on $SiO_2/Al_2O_3$, is 5-600.

9. The preparation process according to claim 7, wherein the molecular sieve precursor has a penta-coordinated aluminium content of 4%-35%.

10. A catalyst comprising a support comprising the molecular sieve according to claim 1 and an active metal component supported on said support, wherein a content of the active metal component, on a basis of elemental metal of the active metal component in a total weight of the catalyst is 0.001 wt %-5 wt %.

11. The catalyst according to claim 10, wherein said active metal component is at least one selected from Group VIII noble metals, ruthenium, osmium, palladium, platinum, rhodium, and iridium.

12. The catalyst according to claim 10, wherein the active metal component is present on the support in a plurality of particles having a size of less than 3 nm.

13. The catalyst according to claim 10, further comprising at least one auxiliary agent component selected from Mg, Ca, Zn, Ti, Fe, Ga, Ge, B, P, and rare-earth metals supported on the support, wherein, on a basis of elemental metal of the at least one auxiliary agent in the total weight of the catalyst, a content of the auxiliary agent is 0.00 1wt %-5 wt %.

14. A process for preparing a catalyst, comprising:

(I) an active metal component precursor and an organic complexing agent are loaded on a support by impregnation, and the resulting material is optionally dried and calcined to produce a semi-finished catalyst; and (II) the semi-finished catalyst obtained in step (I) is impregnated by using a solution containing an organic complexing agent as impregnation liquor, and then dried, wherein: said active metal component is at least one selected from Group VIII noble metals, ruthenium, osmium, palladium, platinum, rhodium, and iridium; said organic complexing agent is at least one selected from an oxygen-containing organic substance, an organic acid and a nitrogen-containing organic substance, ethylene glycol, glycerol, polyethylene glycol, diethylene glycol, butylene glycol, acetic acid, maleic acid, oxalic acid, aminotriacetic acid, 1,2-cyclohexane diamine tetraacetic acid, citric acid, tartaric acid, malic acid, ethylene diamine, and EDTA; the calcination temperature is 350-500° C.; the calcination time is 0.5-8 hours; relative to the weight of the support to be impregnated, in term of element content, the amount of the active metal component precursor is 0.001 wt %-5 wt %; and said support comprises the molecular sieve according to claim 1.

15. The process for preparing the catalyst according to claim 14, further comprising a step of impregnation with a solution of one or more metal ions of one or more metals selected from Mg, Ca, Zn, Ti, Fe, Ga, Ge, B, P, and rare-earth metals.

16. A hydroisomerization treatment method, comprising reacting a hydrocarbon feedstock in presence of the catalyst according to claim 10.

17. The preparation process of claim 7, wherein the wet filter cake has a chemical composition formula of $Al_2O_3$:$SiO_2$:template agent:water, wherein the molar ratio of $Al_2O_3$ to $SiO_2$ is 1:(20-100) and the molar ratio of $Al_2O_3$ to the template agent is 1:(0.001-10).

* * * * *